United States Patent
Miyamoto et al.

(10) Patent No.: US 7,785,333 B2
(45) Date of Patent: Aug. 31, 2010

(54) OVERTUBE AND OPERATIVE PROCEDURE VIA BODILY ORIFICE

(75) Inventors: Manabu Miyamoto, Tokyo (JP); Takumi Dejima, Tokyo (JP); Ken Yamatani, Tokyo (JP); Kiyotaka Matsuno, Sagamihara (JP); Saori Takeuchi, Tokyo (JP); Takahiro Kogasaka, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1021 days.

(21) Appl. No.: 11/358,257

(22) Filed: Feb. 21, 2006

(65) Prior Publication Data

US 2007/0198000 A1     Aug. 23, 2007

(51) Int. Cl.
  A61B 17/04  (2006.01)
  A61B 17/12  (2006.01)
  A61B 1/00   (2006.01)

(52) U.S. Cl. ............... 606/144; 606/148; 606/139; 600/104

(58) Field of Classification Search ........... 604/317, 604/523, 104; 606/144, 139, 148; 600/104
See application file for complete search history.

(56) References Cited

U.S. PATENT DOCUMENTS

| | | | |
|---|---|---|---|
| 3,670,721 A | | 6/1972 | Fukami et al. |
| 4,196,736 A | | 4/1980 | Watanabe |
| 4,362,160 A | | 12/1982 | Hiltebrandt |
| 4,841,888 A | * | 6/1989 | Mills et al. .......... 112/169 |
| 5,041,129 A | * | 8/1991 | Hayhurst et al. .......... 606/232 |
| 5,297,536 A | | 3/1994 | Wilk |
| 5,342,303 A | * | 8/1994 | Ghaerzadeh .......... 604/102.01 |
| 5,417,699 A | | 5/1995 | Klein et al. |
| 5,437,665 A | | 8/1995 | Munro |
| 5,458,131 A | | 10/1995 | Wilk |

(Continued)

FOREIGN PATENT DOCUMENTS

EP     1 518 507 A1     3/2005

(Continued)

OTHER PUBLICATIONS

U.S. Office Action dated Oct. 26, 2009.

(Continued)

*Primary Examiner*—Tatyana Zalukaeva
*Assistant Examiner*—Susan Su
(74) *Attorney, Agent, or Firm*—Scully, Scott, Murphy & Presser, P.C.

(57) ABSTRACT

An overtube includes an insertion portion that has a distal end portion and a proximal end portion, and at least the distal end portion thereof is inserted into a subject; a first lumen that is formed in the insertion portion and that allows freely inserting and removing a device for carrying out medical procedures in the subject; puncture needles that pass through the insertion portion, have a control member connected to the proximal end portion of the insertion portion, and puncture tissue; and second lumens that are provided in the insertion portion and through which puncture needles are passed, the second lumens having on the distal end portion of the insertion portion openings through which distal ends of the puncture needles extend and retract, and the openings being provided on an inside of the insertion portion defined by the first lumen.

11 Claims, 23 Drawing Sheets

U.S. PATENT DOCUMENTS

| | | | |
|---|---|---|---|
| 5,591,179 A * | 1/1997 | Edelstein | 606/144 |
| 5,632,717 A | 5/1997 | Yoon | |
| 5,643,293 A | 7/1997 | Kogasaka et al. | |
| 5,700,273 A * | 12/1997 | Buelna et al. | 606/148 |
| 5,792,153 A | 8/1998 | Swain et al. | |
| RE36,020 E * | 12/1998 | Moore et al. | 606/144 |
| 5,935,107 A | 8/1999 | Taylor et al. | |
| 5,938,668 A * | 8/1999 | Scirica et al. | 606/145 |
| 5,954,732 A * | 9/1999 | Hart et al. | 606/144 |
| 5,984,917 A | 11/1999 | Fleischman et al. | |
| 6,071,263 A * | 6/2000 | Kirkman | 604/104 |
| 6,245,079 B1 | 6/2001 | Nobles et al. | |
| 6,319,263 B1 * | 11/2001 | Levinson | 606/144 |
| 6,402,740 B1 | 6/2002 | Ellis et al. | |
| 6,491,707 B2 | 12/2002 | Makower et al. | |
| 6,517,498 B1 | 2/2003 | Burbank et al. | |
| 6,551,329 B1 * | 4/2003 | Kortenbach et al. | 606/144 |
| 6,638,234 B2 | 10/2003 | Burbank et al. | |
| 6,689,130 B2 | 2/2004 | Arai et al. | |
| 6,837,846 B2 | 1/2005 | Jaffe et al. | |
| 2001/0049497 A1 | 12/2001 | Kalloo et al. | |
| 2002/0022851 A1 | 2/2002 | Kalloo et al. | |
| 2002/0165589 A1 | 11/2002 | Imran et al. | |
| 2003/0130560 A1 | 7/2003 | Suzuki et al. | |
| 2003/0229296 A1 | 12/2003 | Ishikawa et al. | |
| 2003/0236535 A1 | 12/2003 | Onuki et al. | |
| 2004/0059350 A1 | 3/2004 | Gordon et al. | |
| 2004/0249392 A1 | 12/2004 | Mikkaichi et al. | |
| 2005/0107663 A1 | 5/2005 | Saadat et al. | |
| 2005/0137453 A1 * | 6/2005 | Ouchi et al. | 600/106 |
| 2005/0250986 A1 | 11/2005 | Rothe et al. | |
| 2005/0288688 A1 | 12/2005 | Sakamoto et al. | |

FOREIGN PATENT DOCUMENTS

| | | |
|---|---|---|
| EP | 1 602 336 A2 | 12/2005 |
| WO | WO 99/44506 | 9/1999 |

OTHER PUBLICATIONS

U.S. Office Action dated Dec. 29, 2009, received in related U.S. Appl. No. 11/371,565.

U.S. Office Action dated Mar. 5, 2010, received in related U.S. Appl. No. 11/649,036.

U.S. Office Action dated Jun. 8, 2010 received in related U.S. Patent Appl. No. 11/435,182.

* cited by examiner

OVERTUBE AND OPERATIVE PROCEDURE VIA BODILY ORIFICE

BACKGROUND OF THE INVENTION

1. Field of the Invention

The present invention relates to an overtube and a method for a medical procedure through a natural orifice using the same.

2. Description of the Related Art

When carrying out medical procedures such as observation and treatment of the internal organs of the human body, laparotic operation is known in which, instead of forming a large incision in the abdominal wall, a plurality of openings are formed in the abdominal wall, instruments such as a laparoscope and forceps are inserted into respective openings, and the procedure is carried out. In this type of operation, because only forming small openings in the abdominal wall is necessary, there is the advantage in that the burden on the patient becomes small.

Over the past few years, a method for further reducing the burden on patients has been proposed wherein a procedure is carried out by inserting a flexible endoscope through a natural orifice of the patient, such as the mouth, nose, or rectum. An example of such a procedure is disclosed in U.S. Pat. No. 5,458,131.

In this method, a flexible endoscope is inserted through the patient's mouth, an incision is formed in the stomach wall, and the distal portion of the endoscope is passed into the abdominal cavity through this opening. In addition, while using the endoscope as an apparatus to observe the inside of the abdominal cavity, the desired procedure is carried out in the abdominal cavity by using instruments that are passed through the endoscope or instruments that are inserted through another opening.

SUMMARY OF THE INVENTION

An object of the present invention is to provide an apparatus and method that enables carrying out more easily the incision of tissue when carrying out medical procedures using an overtube.

An overtube according to a first aspect of the present invention has an insertion portion that has a distal end portion and a proximal end portion, and at least the distal end portion thereof is inserted into a subject; a first lumen that is formed in the insertion portion and that allows freely inserting and removing a device for carrying out medical procedures in the subject; puncture needles that pass through the insertion portion, have a control member connected to the proximal end portion of the insertion portion, and puncture tissue; and second lumens that are provided in the insertion portion and through which puncture needles are passed, the second lumens having on distal end portion of the insertion portion openings through which distal ends of the puncture needles extend and retract, and the openings being provided on an inside of the insertion portion defined by the first lumen.

An overtube according to a second aspect of the present invention has an insertion portion that has a distal end portion and a proximal end portion and that has formed therein a first lumen that allows inserting and removing a device for carrying out medical procedures in a subject, and at least the distal end portion thereof is inserted into a subject; puncture needles that puncture tissue pass through the insertion portion and that have a control member connected to the proximal end portion of the insertion portion; and second lumens that are provided in the insertion portion and through which puncture needles pass, the second lumens having on the distal end portion of the insertion portion openings through which distal ends of the puncture needles extend and retract, and the openings being provided on an inside of the insertion portion that forms the first lumen.

An method for a medical procedure through a natural orifice according to a third aspect of the present invention includes: inserting an overtube through a natural orifice of a subject, the overtube having a lumen formed therein that allows passage of a device; projecting the puncture needles that is passed through the overtube from an inside of the overtube defined by the lumen; and puncturing tissue by the puncture needles while observing the puncture needles by using an observation apparatus inserted into the lumen.

DETAILED DESCRIPTION OF THE INVENTION

Figure 1:
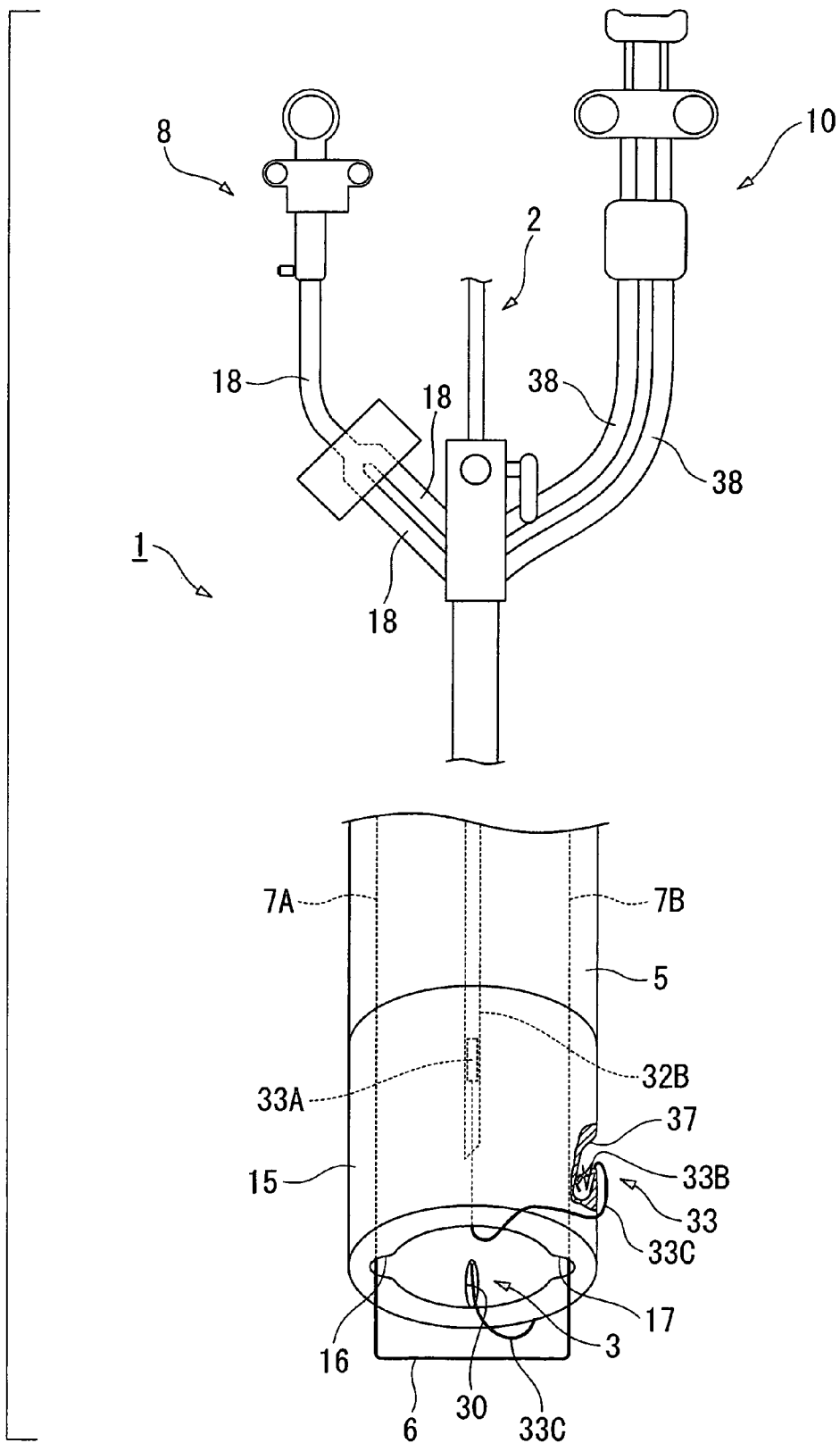
FIG. 1 is a schematic drawing showing the entire overtube according to a first embodiment.

The embodiments are explained in detail below. Note that below, identical structural elements are denoted by identical reference numerals, and redundant explanations thereof are omitted.

First Embodiment

The overtube 1 according to the present embodiment provides a device insertion portion which is inserted into the body of a subject of an examination, and is used as a guide tube when inserting into the body a device such as an endoscope (in order to simplify the explanation, in the following explanation this may simply referred to as a "device" or an "endoscope") for performing medical procedures in the body. Note that the content of the medical procedures may include a variety of procedures, such as suturing, observation, incision, and cell aspiration. More specifically, other examples include the observation of the abdominal organs, biopsies of the liver and pancreas, cauterizing myoma of the uterus and liver (and other organs), contraceptive therapies, extracting the appendix and gallbladder, and obesity operation.

As shown in FIG. 1, this overtube 1 has an insertion portion 5 that has a first lumen 3 having a distal end that opens in the direction of insertion into the subject and into which an endoscope 2, which is an example of a device that extends in an axial direction, is inserted so as to be freely removable, and is inserted into a luminal organ such as the stomach or the abdominal cavity of a patient; a cutting electrode (tissue cutting portion) 6 that traverses the distal end side of the first lumen 3 and, in the traversing state, is releasably disposed in the insertion portion 5, and cuts the body tissue of the patient; electrode controlling wires (controlling members) 7A and 7B that are each connected to the cutting electrode and disposed so as to be freely extendable and retractable in the insertion portion 5; a electrode controlling portion (operating portion) 8 that extends or retracts the electrode controlling wires 7A and 7B in the first lumen 3; and a needle control portion 10 for controlling the puncture needles 32A and 32B and the pushers 35 described below. Note that in this embodiment, the cutting electrode 6 and the electrode controlling wires 7A and 7B are formed by one wire. However, the cutting electrode 6 and the electrode controlling wires 7A and 7B may be formed by separate members and connected together.

Figure 2:
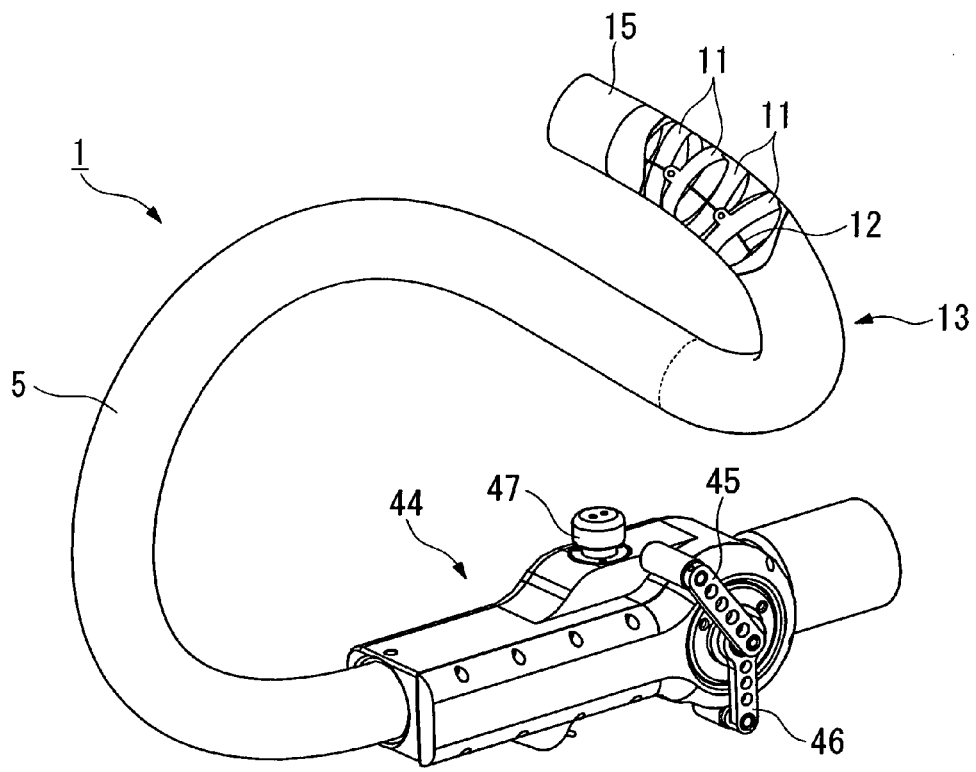
FIG. 2 is a drawing showing the essential portions of the overtube according to a first embodiment.
Figure 3:
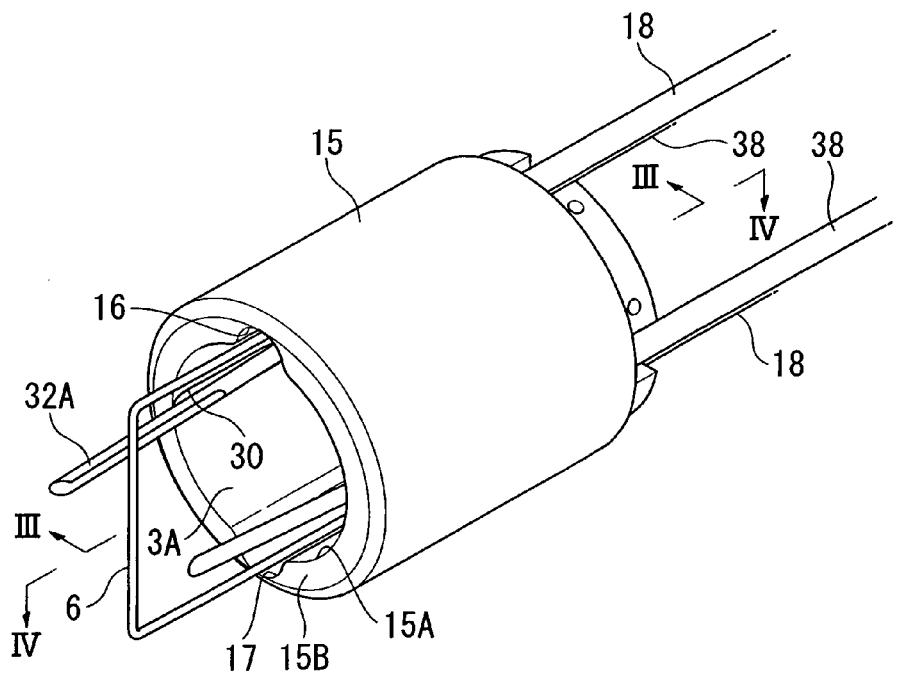
FIG. 3 is a perspective view showing the distal end of the overtube according to a first embodiment.

As shown in FIG. 2, the insertion portion 5 is elongated and flexible, and like a typical flexible endoscope, a bending portion 13 is provided at the distal end side of the insertion portion 5. In the bending portion 13, a plurality of segmenting rings 11 are connected along the bending wires 12. Here, a bending portion 13 that is actively bent by the operation of the operator is not provided. Rather the insertion portion may be formed in the shape of a flexible tube and passively bent by following the bent shape of a device such as an endoscope. As shown in FIG. 3, a short tubular distal end portion 15 is provided farther toward the distal end than the bending portion 13. The distal end 15 is formed by a substantially colorless transparent material such as polycarbonate, and the visibility is improved thereby in comparison to the case of being manufactured by an opaque material. Note that the distal portion of the distal end portion 15 (the portion of the distal end at which the opening of the first lumen 3 is formed) forms an abutting portion 15B that abuts the tissue.

The cutting electrode 6 is a wire made, for example, of stainless steel and capable of high frequency conduction. During an incision in which the tissue is cut (first state), the cutting electrode 6 is disposed so as to traverse the center portion of the first lumen 3 in a direction perpendicular to the axial direction of the insertion portion 5. The length of the cutting electrode 6 is formed so as to be longer than the inner diameter of the first lumen 3. That is, as shown in the state of use in FIG. 3, one end of the cutting electrode 6 is disposed in the first inner groove 16 that is formed in the outer edge of the first lumen 3 (in other words, the inner peripheral surface or inside of the distal portion 15 that defines the first lumen 3), which is the inner surface of the distal end portion 1. The other end of the cutting electrode 6 is disposed in the second inner groove 17 formed in the outer edge (in other words, the inner peripheral surface or inside of the distal end portion 15 that defines the first lumen 3) at a substantially symmetrical position with respect to the first inner groove 16 across the center of the first lumen 3.

As shown in the accommodated state (second state) in FIG. 4, one end of the cutting electrode 6 is connected to the electrode controlling wire 7A. The other end of the cutting electrode 6 is connected to the electrode controlling wire 7B. Each of the electrode controlling wires 7A and 7B passes so as to be freely extendable and retractable in the electrode tubes 18, which consist of an insulator. The electrode tubes 18 are routed through the inside of the insertion portion 5 from the proximal side. As shown in FIG. 4, the distal ends of the electrode tubes 18 abut the steps 16A and 16B formed in the corresponding inner grooves 16 and 17 of the distal end portion 15. In this embodiment, one wire is used for the cutting electrode 6 and the electrode controlling wires 7A and 7B, and the diameter of the portion that forms the cutting electrode 6 is formed so as to be narrower than the diameter of the portion that forms the electrode controlling wires 7A and 7B. However, this is not limiting, and the cutting electrode 6 and the electrode controlling wires 7A and 7B may be formed by separate members. In addition, the diameters of the cutting electrode 6 and the electrode control wires 7A and 7B may be identical.

In the accommodation state shown in FIG. 4, the cutting electrode 6 is accommodated in the accommodating portion 90 formed on the inner peripheral surface of the distal end 15. The accommodating portion 90 is a groove that is provided from the first inner groove 16 to the second inner groove 17 along the peripheral direction. The end portion of the accommodating portion 90 is disposed slightly closer to the distal end than the steps 16A and 16B that abut the electrode tubes 18.

Figure 5:
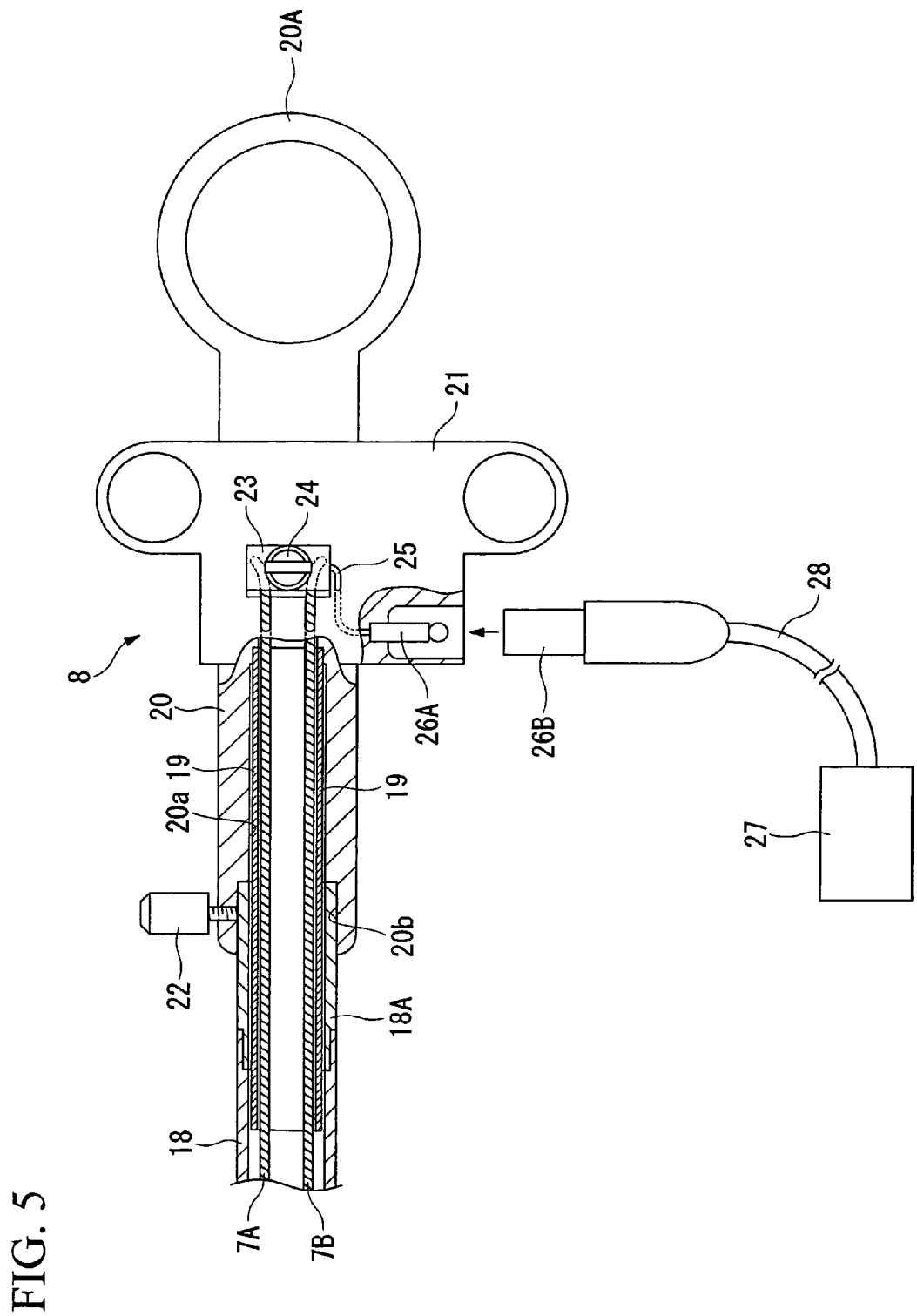
FIG. 5 is a partial enlarged cross-sectional view showing the electrode control portion of the overtube according to a first embodiment.

Note that, as shown in FIG. 1 and FIG. 5, there is one electrode tube 18 at the proximal end that projects from the insertion portion 5, but in order to accommodate the electrode controlling wires 7A and 7B separately in the insertion portion 5, the two wires are separated along the way and inserted into the insertion portion 5, and the distal ends are connected to the distal end portion 15. The proximal ends of the electrode controlling wires 7A and 7B pass through the one rigid operating pipe 19 that is disposed so as to project from the distal end of a control handle 21 described below.

The electrode controlling portion 8 has an control body portion 20 that is connected to the proximal end of a electrode tube 18 and a control handle 21 that is disposed on the control body portion 20 so as to be freely extendable and retractable. A through hole 20a is provided through which the electrode controlling wires 7A and 7B and the operating pipe 19 are inserted. An engaging hole 20b that engages the rigid portion 18A, which is disposed at the proximal end of the electrode tube 18, is formed on the distal end of the controlling body portion 20, and the electrode tube 18 is fastened to the engaging hole 20b by a screw 22. A finger grasping portion 20A is disposed at the proximal end of the control body portion 20.

A connecting plate 23 is disposed on the control handle 21, and is electrically connected to the end portion of the electrode controlling wires 7A and 7B that have been passed through the operating pipe 19. A fastening screw 24 is disposed on the connecting plate 23, and by clamping the fastening screw 24 onto the connecting plate 23, the electrode controlling wires 7A and 7B are fastened and electrically connected. The connecting plate 23 is electrically connected to the connecting terminal 26A that is disposed on the control handle 21 via the electric wiring 25. A connecting terminal 26B that is disposed on the distal end of a power cord 28, which extends from the high frequency power source 27, is fastened to and released from the connecting terminal 26A. A finger grasping portion 21A is also disposed on the control handle 21.

Figure 4A:
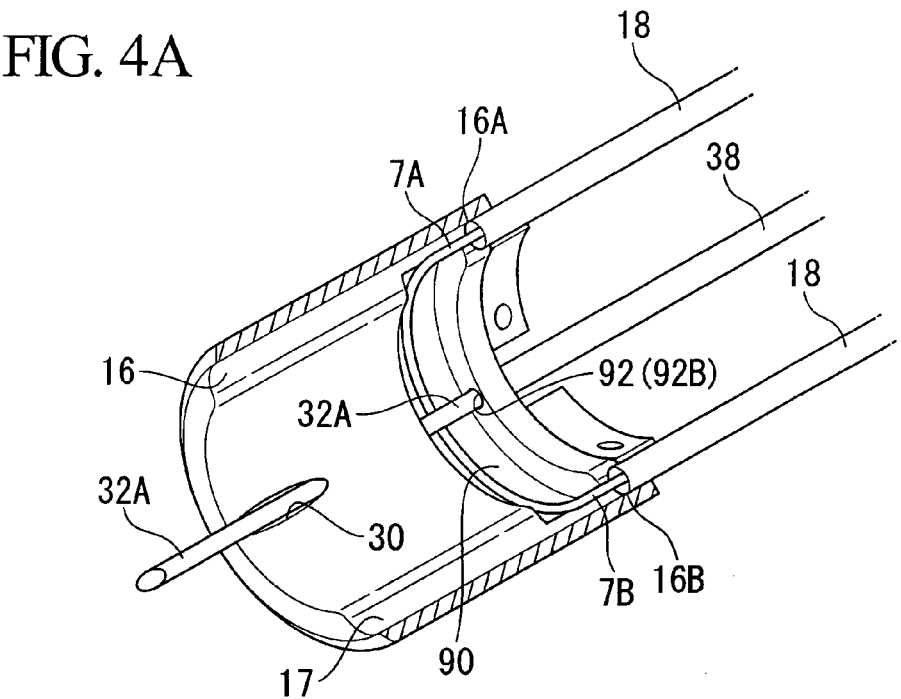
FIG. 4A is a cross-sectional view along III-III in FIG. 3.
Figure 4B:
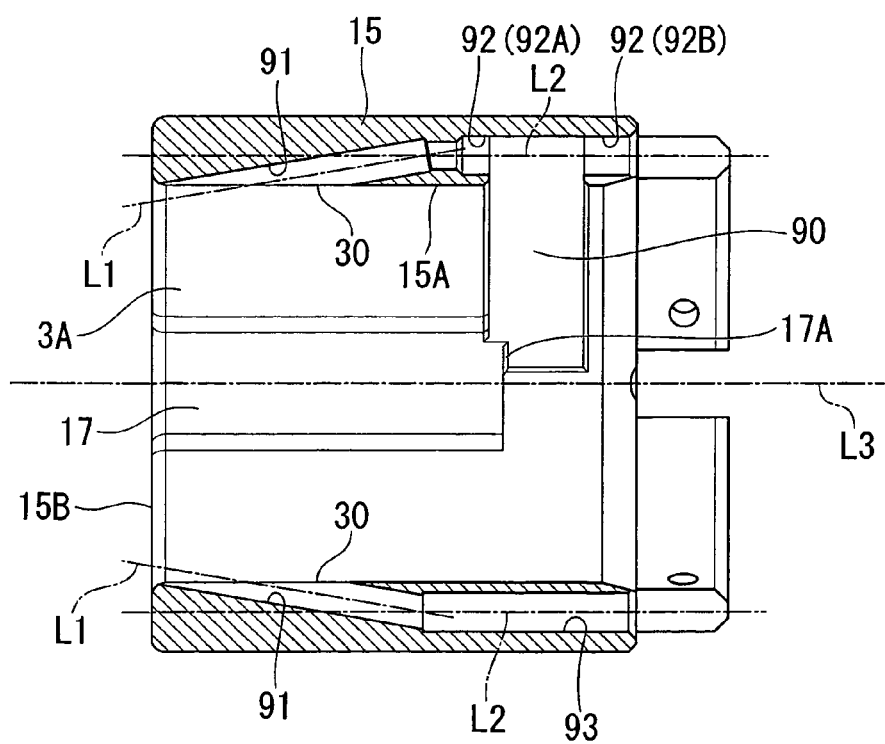
FIG. 4B is a cross-sectional view along IV-IV in FIG. 3.

As shown in FIG. 4B, on the inner peripheral surface 15A of the distal end 15 of the overtube 1, long holes 30 are each formed having a long axis in the longitudinal direction (the direction that join the distal end and the proximal end of the insertion portion 5) of the distal end portion 15 in a position substantially perpendicular to the direction in which the first inner groove 16 and the second inner groove 17 are connected. The long holes 30 serve as the distal end opening (the opening from which the puncture needles 32A and 32B project) of the needle lumens 92 and 93 through which the puncture needles 32A and 32B pass. In this embodiment, the center of the long holes 30 is provided more toward the proximal end side than the distal end opening 3A of the distal end portion 5. The long holes 30 communicate with the guide portions 91 that form the lumens through which the puncture needles 32A and 32B pass, and the guide portions 91 are formed so as to incline inside the distal end portion 15. The proximal end sides of the each of the guide portions 91 form conduits that communicate with the distal ends of each of the needle lumens 92 and 93 formed on the proximal end portion of the distal end portion 15, thereby forming a second lumen along with the needle lumens 92 and 93. The center axes of the needle lumens 92 and 93 are formed substantially parallel to the axis L3 (also referred to as the center axis) of the first lumen 3, and are provided at opposing positions across the approximate center of the first lumen 3, and are formed mutually parallel in their longitudinal direction. The axes (center axes) L1 of guide portions 91 are inclined inward (on the axis of the first lumen (or on the center axis of the first lumen 3)) at an angle of 5° to 15° with respect to the axis of the needle lumens 92 and 93. Note that the needle lumen 92 is provided at a location that crosses with the accommodating portion 90 for the cutting electrode 6 described above. Therefore, the needle lumen 92 is partitioned into a portion 92A more toward the distal end side than the accommodating portion 90 and a portion 92B that is more toward the proximal end side than the accommodating portion 90. The external sheaths 38 pass through the portion 92B and the needle lumen 93. The distal end of the external sheaths 38 respectively abut the distal end portion of the needle lumen 93 and the distal end portion of the portion 92B, and are thereby connected and fastened.

The puncture needles (hollow needles) 32A and 32B pass through the inside of the external sheaths 38 so as to be freely extendable and retractable. Inside the puncture needles 32A and 32B, pushers 35 are disposed so as to be freely extendable and retractable. One end of a flexibly deformable coil sheath is connected to the proximal end of the puncture needles 32A and 32B, and pusher operating wires that operate the pushers 35 pass inside the coil sheath. The other end of the coil sheath extends toward the proximal end side of the insertion portion 5, and communicates with a needle control portion 10.

Figure 7:
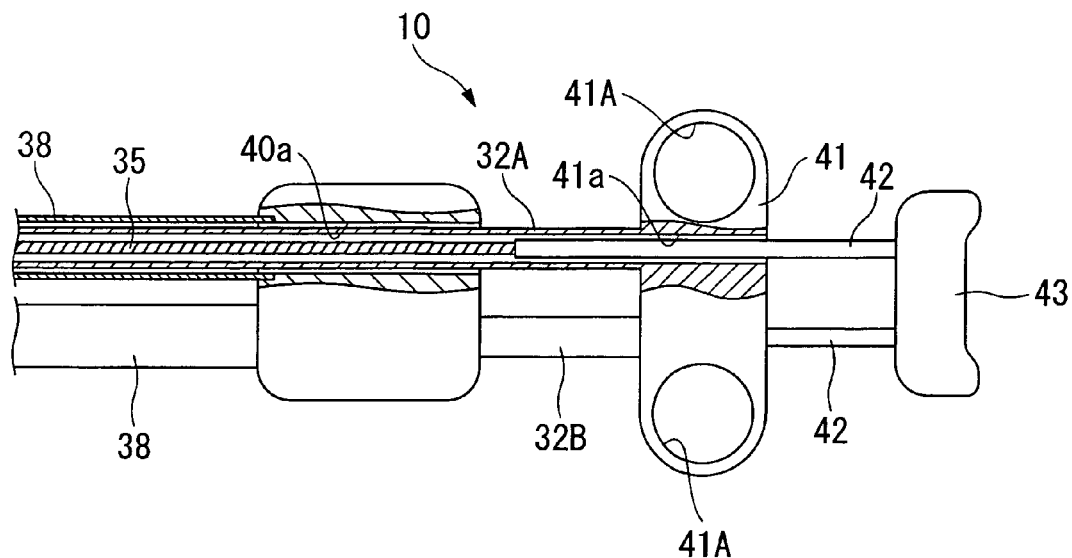
FIG. 7 is a partial cross-sectional view showing the needle control portion of the overtube according to a first embodiment.

As shown in FIG. 1 and FIG. 7, the needle control portion 10 has a sheath grip portion 40 that is disposed so as to connect to the proximal ends of the two external sheaths 38; a needle control handle 41 that is disposed so as to connect to the proximal end of the two puncture needles 32A and 32B that have been passed through the through holes 40a provided in the sheath grip portion 40 so as to be freely extendable and retractable; and a pusher connecting portion 43 that is connect to the end portions of the rod-shaped rigid portions 42 connected to the proximal end of the two pushers 35 that pass through the through holes 41a provided on the needle control handle 41 so as to be freely extendable and retractable. The finger grasping portion 41A is provided in the needle control handle 41. Note that the needle control handle 41 and the pusher connecting portion 43 may be partitioned into two such that the two puncture needles 32A and 32B and the two pushers 35 operate independently of each other.

Here, a slit 32a is formed at the distal ends of the puncture needles 32A and 32B, and a rigid pressing member 35A is disposed on the distal end of the pushers 35. In the puncture needles 32A and 32B, as shown in FIG. 6B, anchors 33A of a two-arm T bar 33 are each held at a portion more to the distal side than the pressing member 35A.

Figure 6A:
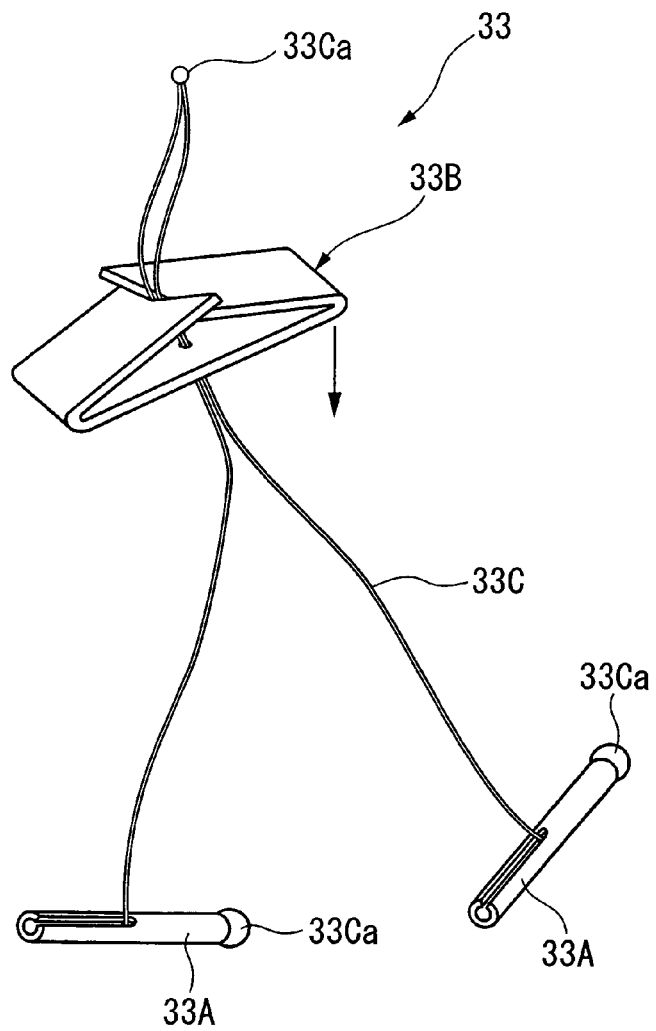
FIG. 6A is an overall view showing the two-armed T bar used in the present embodiment.

As shown in FIG. 6A, the two-arm T bar 33 has two sutures 33C that each pass through one end side in a substantially triangular shaped stopper 33B. In addition, the two sutures 33C may be formed by one thread. In this case, the large diameter portion 33Ca can be formed by tying a knot along the one thread. Furthermore, a loop may be formed at the proximal end portion of this knot, and thereby the proximal end side is easily retained by an instrument or the like. When formed by one suture, there is the merit that the strength can be increased in comparison to the case in which two sutures are tied together.

One end of the sutures 33C is formed into a large diameter portion 33Ca by tying both end portions together. The anchors 33A are respectively fastened to the other ends of each of the sutures 33C. The anchors 33A have a cylindrical shape with a slit formed at the end portion, and the sutures 33C are passed in the longitudinal direction into the anchors 33A through the slits of the anchors 33A. The large diameter portion 33Ca having a diameter that is larger than the anchors 33A is formed on the other end of the sutures 33C. The stopper 33B has a hole at the center of an elongated plate member in the longitudinal direction, and the sutures 33C pass through this hole. Both end portions of the stopper 33B in the longitudinal direction are bent back at an angle to fasten the sutures 33C. Both end portions of the stopper 33B in the longitudinal direction are cut into triangular shaped notches. The stopper 33B fastens the sutures 33C by both end portions being bent back at an angle such that the notches intersect. Thereby, the sutures 33C will not fall out from between the end portions. When the large diameter portion 33Ca of the sutures 33C is pulled away from the stopper 33B, both end portions of the stopper 33B open slightly. Thereby, the stopper 33B permits movement of the sutures 33C in this direction. In contrast, when a large diameter portion 33Ca of the sutures 33C on the anchor 33A side is pulled, the sutures 33C move in the direction shown by the arrow in FIG. 6A. However, at this time, the sutures 33C do not move because both end portions of the stopper 33B close to clamp the sutures 33C.

Figure 6B:
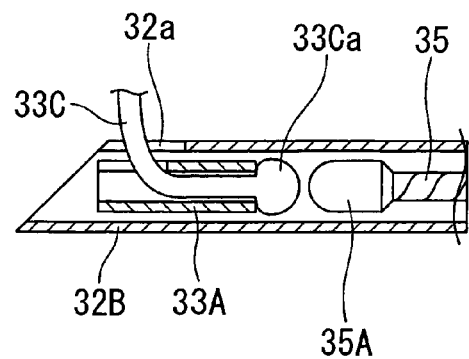
FIG. 6B is a cross-sectional view showing the state in which the two-arm bar is mounted on the puncture needle of the overtube according to a first embodiment.

As shown in FIG. 6B, the pushers 35 are disposed inside each of the puncture needles 32A and 32B so as to be freely extendable and retractable. As shown in FIG. 1, the stoppers 33B of the two-armed T part 33 are accommodated in a hole 37 (below, simply referred to as a hole) formed in the side surface of the insertion portion 5 from the proximal end side toward the distal end side.

As shown in FIG. 2, a proximal handle 44 having a diameter larger than the insertion portion 5 is disposed at the proximal end of the insertion portion 5 of the overtube 1. The proximal handle 44 has disposed thereon a bending control lever 45 that is connected to the proximal end side of the bending wire 12 and carries out the bending control of the bending portion 13; a bending lock lever 46 that fastens the position of the bending control lever 45 at an arbitrary position; and an endoscope lock button 47 that fastens the endoscope 2 in the first lumen 3 when the endoscope 2 is passed through the first lumen 3.

The distal end sides of the bending wires 12 are fastened to the distal end portion 15, and in this embodiment, two bending wires 12 pass through the inside of the insertion portion 5, and the distal ends thereof are fastened at substantially opposing positions of the distal end portion 15 across the center of the first lumen 3. Note that in this embodiment, two bending wires 12 are provided and the bending portion 13 is formed so as to bend in two directions. However, this is not limiting, and like the bending portions of well-known endoscopes, a structure may be used wherein four bending wires 12 and two bending control levers 45 are provided, and the bending portion bends in four dictions.

Figure 8:
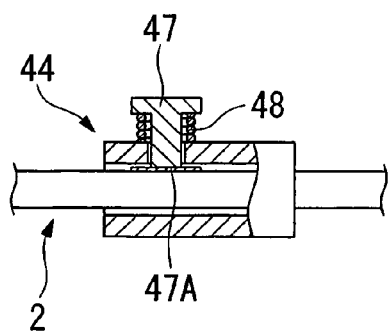
FIG. 8 is a cross-sectional view of the vicinity of the endoscope lock button of the overtube according to a first embodiment.

As shown in FIG. 8, a broad pressing portion 47A is disposed at the distal end of the endoscope lock button 47, and during normal usage, the endoscope lock button 47 is urged outward by the spring 48 in the radial direction of the proximal handle 44. When it is necessary to insert and fasten the endoscope 2 inside the insertion portion 5, the endoscope lock button 47 is pressed inward in the radial direction, and thereby the pressing portion 47A presses the endoscope 2 so that the endoscope 2 is relatively fastened due to friction. Note that alternately the endoscope lock button 47 may be pressed to release the friction. In addition, a mechanism may be provided in which the endoscope is locked while the pressing portion 47A is pressed inward in the radial direction, and the endoscope 2 and the insertion portion 5 are maintained in a fastened state when the finger has removed from the pressing portion 47A.

Figure 9:
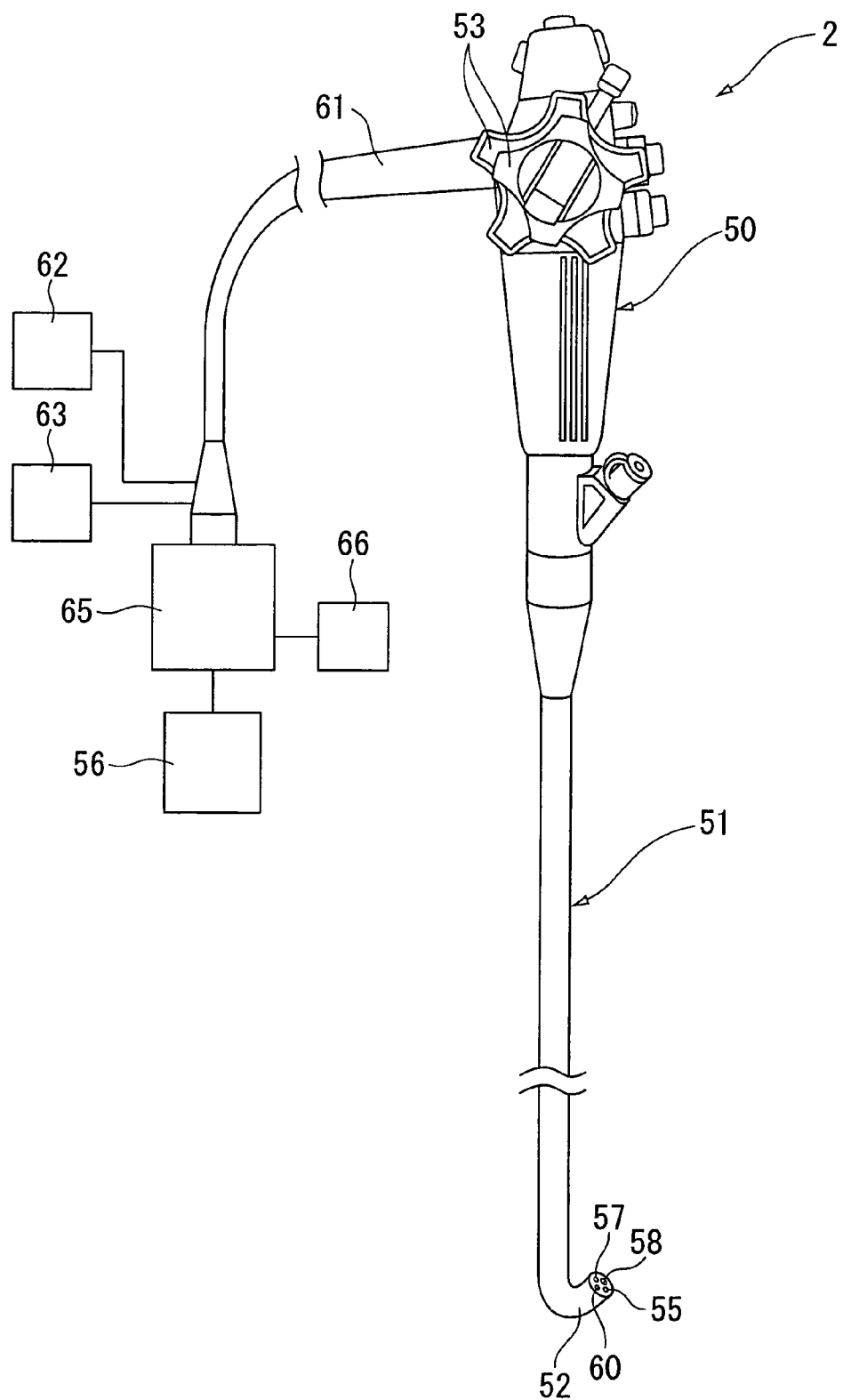
FIG. 9 is an overall schematic view of the endoscope showing an example of the device used in the overtube according to a first embodiment.

As shown in FIG. 9, the endoscope 2 that has been inserted into this overtube 1 is, for example, a flexible endoscope, and an elongated flexible endoscope insertion portion 51 that is inserted into the body of a patient extends from the endoscope control portion 50, which is operated by a technician. The endoscope distal end portion 52 of the endoscope insertion portion 51 can be bent by operating the angle knob 53 disposed on the endoscope control portion 50. An observation apparatus 55, a distal end surface of an optical fiber 57 that guides light from a light source apparatus 56 disposed outside the body, and a distal end opening of the channels 58 and 60 are provided in the endoscope distal end portion 52. The channel 58 is a passage that is connected to a gas and water feeding apparatus 62 and a suction apparatus 63 that are disposed outside the body via a universal cable 61. The channel 58 is used for supplying and aspirating fluids within the body. In addition, the channel 60 is a passage for inserting and retracting instruments, and is disposed between the 6 o'clock and the 8 o'clock positions of the endoscope insertion portion 51. Note that, for example, two channels for the instruments may be provided, and the invention is not limited to a single channel. Observation images captured by the observation apparatus 55 are displayed on a monitor 66 via a control portion 65.

Figure 10:
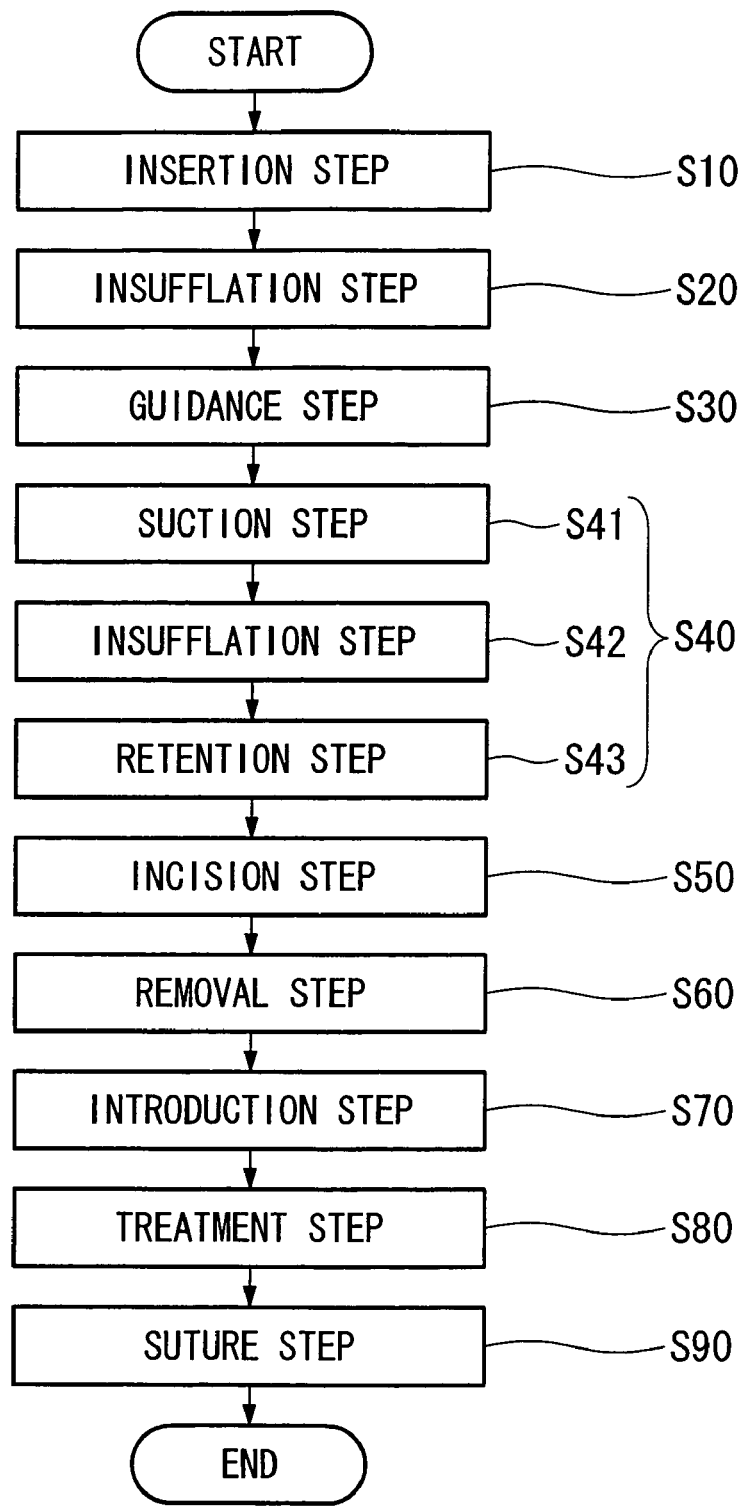
FIG. 10 is a flowchart showing the medical procedure according to a first embodiment.

Next, the operation of the present embodiment will be explained along with a method for a medical procedure through a natural orifice shown in the flowchart in FIG. 10 using the overtube 1. Note that in the following, the targeted incision site T is on the anterior wall of the stomach ST, and a procedure is explained in which a medical procedure is carried by inserting the endoscope 2 through the mouth M of the patient PT into the stomach (abdominal organ) ST and then inserting the insertion portion 5 of the endoscope 2 into the abdominal cavity AC through opening the stomach wall. In addition, in the embodiment explained below, the endoscope 2 is inserted as a device through the mouth M of the patient PT into the body, and the abdominal cavity AC is approached by forming an opening SO in the anterior wall of stomach ST. However, the natural orifice into which the endoscope 2 is inserted is not limited to the mouth M, and the natural orifice may be the rectum, nose, or the like. Furthermore, preferably an opening SO is formed in the anterior wall of the stomach ST. However, this is not limiting, and an opening in the wall of a luminal organ (hollow organ) into which the device may be inserted as a natural orifice may be formed in another part of the stomach ST, the esophagus, the small intestine, the large intestine or the like.

First, as a preparatory step, the electrode controlling wires 7A and 7B are passed through the electrode tubes 18, and the cutting electrode 6 is disposed at the distal end portion 15. A jig (not illustrated) is inserted into the distal end opening 3A of the distal end portion 15 and the cutting electrode 6 pressed and inserted into the accommodation portion 90. In this state, the puncture needles 32A and 32B are passed through the external sheath 38. As shown in FIG. 4A, the puncture needle 32A traverses the accommodation portion 90, and the cutting electrode 6 is disposed between the puncture needle 32A and the inner peripheral wall of the accommodation portion 90. The puncture needle 32A that traverses the accommodation portion 90 serves as an engaging portion, and thereby the cutting electrode 6 is inhibited from projecting into the first lumen 3. When this action has finished, the jig (not illustrated) is extracted.

When the medical procedure is carried out, the endoscope (device) 2 is passed through the first lumen 3 disposed in the insertion portion 5 of the overtube 1, and the overtube 1 is inserted up to the proximal end side of the endoscope insertion portion 51. In this state, first the endoscope insertion portion 51 is inserted into the body of the patient PT, who is facing upwards, and next the overtube 1 is inserted into the body to guide the endoscope insertion portion 51. In this manner, an insertion step (S10) is carried out in which the insertion portion 5 of the overtube 1 and the endoscope 2 are inserted. By carrying out such an insertion step, when the endoscope 2 is first inserted into the body, it is possible to insert the endoscope 2 alone into the body, and thus the insertion characteristics are improved.

Figure 11:
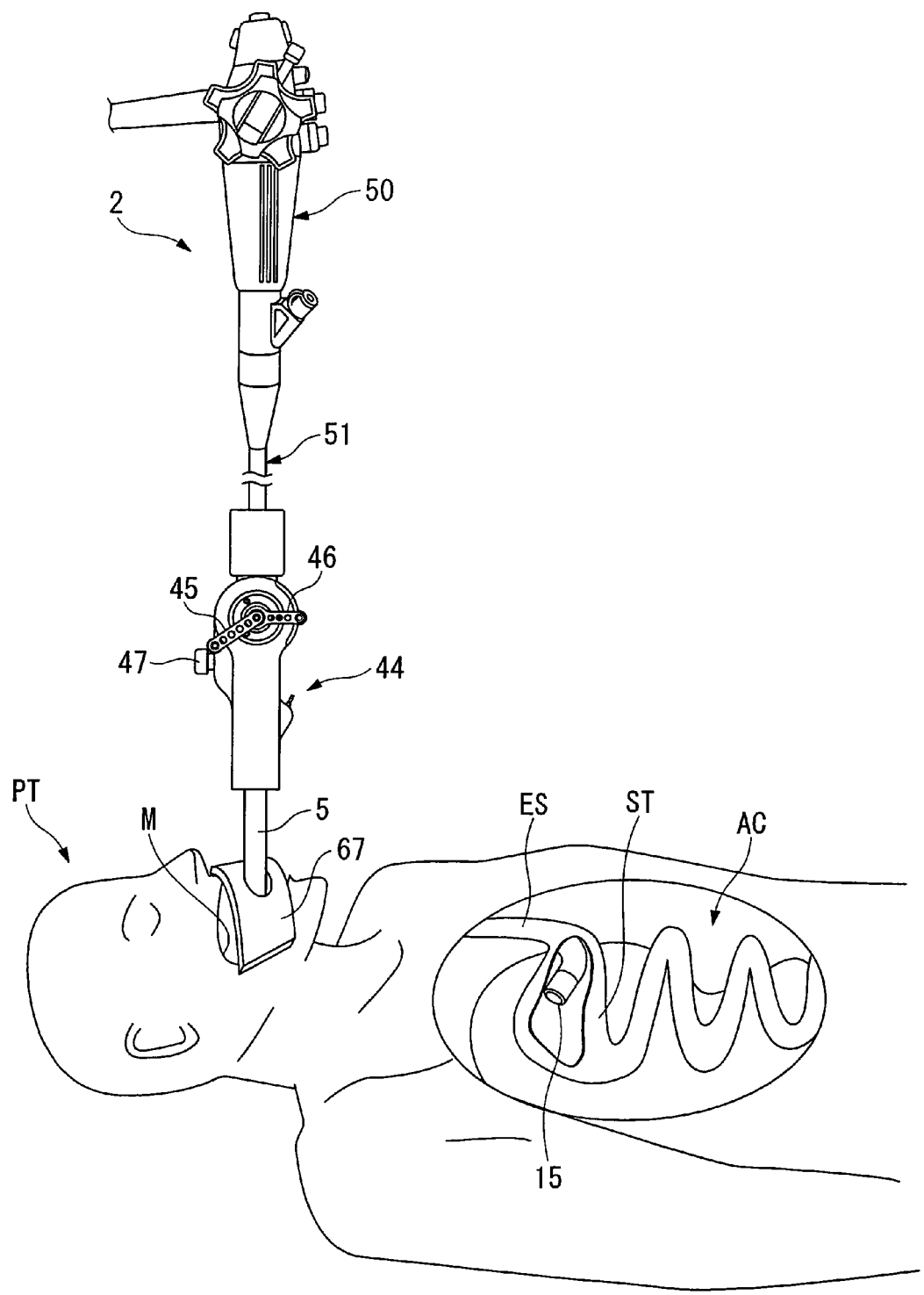
FIG. 11 is a drawing for explaining the state in which the endoscope is inserted into the overtube during a medical procedure according to a first embodiment.

As shown in FIG. 11, a mouth piece 67 is affixed to the mouth of the patient PT, and with the endoscope 2 inserted into the first lumen 3 into the esophagus ES, the overtube 1 and the endoscope 2 are inserted through the mouth piece 67. Note that the cutting electrode 6 and the puncture needles 32A and 32B do not project into the first lumen 3 of the distal end portion 15, and thus it is possible to prevent interference between cutting electrode 6, the puncture needles 32A and 32B, and the endoscope 2. Then, when the overtube 1 and the endoscope 2 are inserted into the body, it is possible to engage the cutting electrode 6 in advance on the inner surface of the first lumen 3. When the endoscope 2 advances relative to the overtube 1, the cutting electrode 6 is not an obstruction, it is possible to project the distal end of the endoscope 2 from the overtube 1, and thereby the characteristics of insertion into the body are improved.

Next, as an insufflation step (S20), air is supplied to the stomach ST via the channel 58 of the insertion portion 5 from the air and water feeding apparatus 62 to distend the stomach ST.

Figure 12:
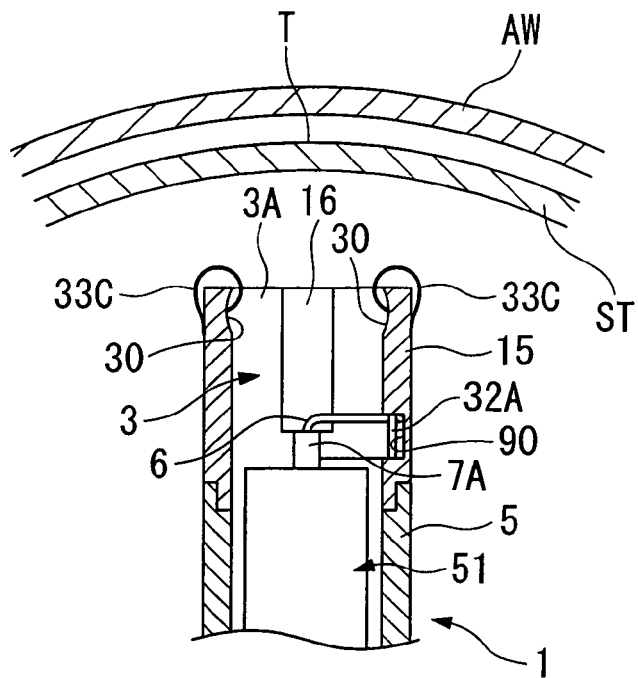
FIG. 12 is a drawing for explaining the state in which the overtube is introduced into the targeted incision site during a medical procedure according to a first embodiment.

Next, while confirming the targeted incision site T by using the endoscope 2, which also serves as an observation device, the processes moves to a guidance step (S30) in which the insertion portion 5 of the overtube 1 is guided up to the targeted incision site T. First, after the endoscope insertion portion 51 of the endoscope 2 has been inserted into the stomach, while observing the interior of the stomach ST via the observation apparatus 55 disposed in the endoscope insertion portion 51, the distal end of the endoscope insertion portion 51 is brought up to the targeted incision site T by operating the angle knob 53. Next, while identifying the targeted incision site T, using the endoscope insertion portion 51 as a guide, the insertion portion 5 of the overtube 1 is pressed, and as shown in FIG. 12, the distal end 15 of the overtube 1 approaches in proximity to the targeted incision site T.

Figure 13:
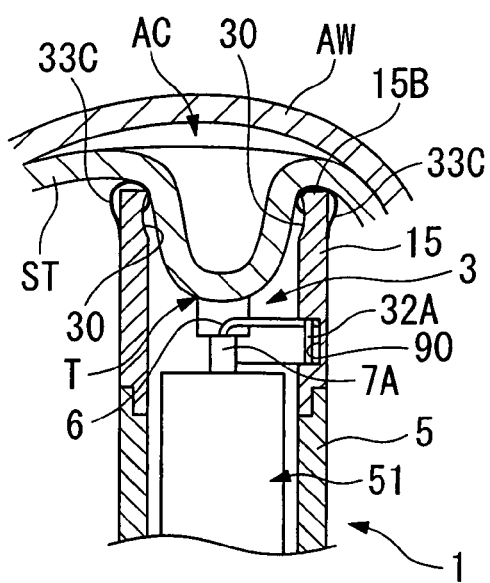
FIG. 13 is a drawing for explaining the state in which a portion of the stomach wall is sucked into the overtube in a medical procedure according to a first embodiment.

Next, the process proceeds to a needle moving step (S40) in which the puncture needles 32A and 32B, which are disposed at the distal end side of the insertion portion 5, are extended and retracted along the first lumen 3. First, as a suction step (S41), while the distal end portion 15 is abutted against the stomach wall so as to include the targeted incision site T, the stomach wall is sucked by the suction apparatus 63 via the channel 58. At this time, as shown in FIG. 13, a portion of the stomach wall is sucked into the first lumen 3 of the distal end portion 15 from the distal end opening 3A. Thereby, a space is established between the outer stomach wall and the abdominal cavity AC. Here, as a device for sucking the stomach wall, a method in which the channel 58 of the endoscope 2 is used is not limiting. For example, a space formed between the inner surface of the first lumen 3 of the overtube 1 and the outer periphery of the insertion portion of a device such as an endoscope 2 that has been inserted into the first lumen 3 may be used as a suction passage, and a suction may be established by being attached to a suction apparatus 63. In this case, the suction effect may be further improved by providing a valve (not illustrated) in the established space to inhibit the flow of fluids between the inside and outside of the body.

Figure 14:
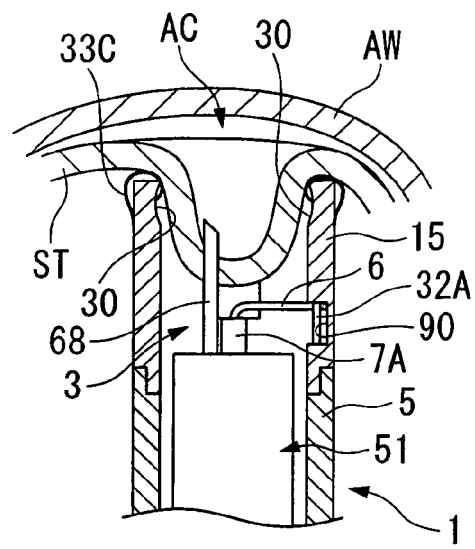
FIG. 14 is a drawing for explaining the state in which the abdominal cavity is insufflated by feeding air from an injection needle during a medical procedure according to a first embodiment.

Next, the process proceeds to a peritoneum insufflation step (S42). First, the peritoneum insufflation needle 68, which is connected to the air and water feeding apparatus 62, is inserted into the channel 60 of the endoscope 2. Then the distal end of the peritoneum insufflation needle 68 is projected into the distal end portion 15, and as shown in FIG. 14, inserted farther up to the abdominal cavity AC by puncturing the sucked stomach wall. Thereby, while the space between the sucked stomach wall and the abdominal wall AW is established, the stomach wall is punctured by the peritoneum insufflation needle 68, and thereby it is possible to puncture only the stomach wall reliably. Next, air is passed into the abdominal cavity AC via the peritoneum insufflation needle 68 and the abdominal cavity AC is inflated so that the stomach ST and the abdominal wall AW are separated.

Preferably, the length of this peritoneum insufflation needle 68 is about 12 mm, and more preferably, the distal end can be bent so as to be able to penetrate the center of the sucked stomach wall. In the case of a bent injection needle, there is a bend at the distal end, and a bent wire (not illustrated) is installed that passes through the inside of the bend in the radial direction from the distal end toward the proximal side. Here, the channel 60 of the endoscope 2 is disposed between the 6 o'clock and the 8 o'clock direction of the endoscope insertion portion 51, and thus when the anterior wall of the stomach ST, the preferable incision position, is cut, the approach is from an upward angle. Therefore, the bent wire faces the center because the bend follows the condition of the bending of the insertion portion 5 of the overtube 1, and thus by pulling the bent wire toward the proximal side, it is possible to puncture the center of the stomach wall reliably. In addition, when using a normal injection needle without a bending capacity, the bending control of the endoscope 2 is carried out in the overtube 1, and the injection needle thereby faces the middle. Note that during insufflation, the inside of the abdominal cavity AC may be maintained at an appropriate pressure by a feed gas pressure monitor and automatic control.

Figure 15:
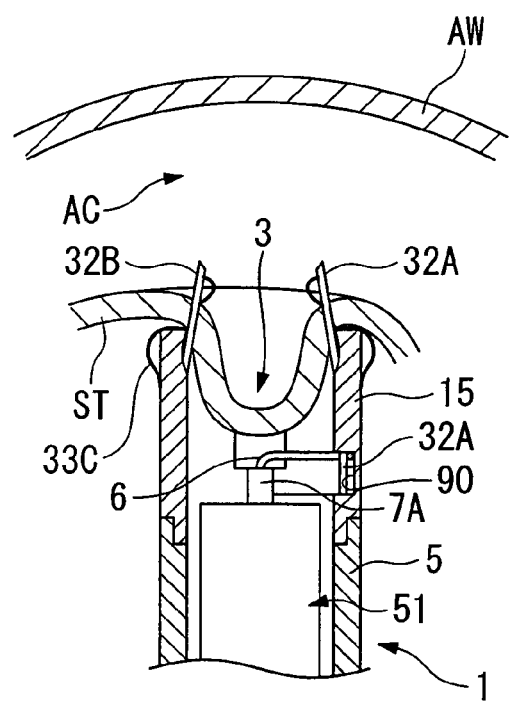
FIG. 15 is a drawing for explaining the state in which the sucked stomach wall is punctured by the puncture needles of the overtube in a medical procedure according to a first embodiment.

Next, the process proceeds to a retention step (S43). Here, first the sheath grip portion 40 is grasped, and the needle control handle 41 is advanced in the direction of the sheath grip portion 40. As shown in FIG. 15, the puncture needles 32A and 32B advance toward the inside (the center of the first lumen 3) along the guiding portion 91, project from the long holes 30, and puncture the portion of the stomach wall that is being sucked. Because a space has been established between the abdominal cavity AC and the stomach wall by insufflation, the puncture needles 32A and 32B puncture only the stomach wall. In addition, the puncture needles 32A and 32B enter the stomach wall toward the inside following the inclination of the guiding portion 91, and thus it is possible to visually confirm the movement of the puncture needles 32A and 32B, the entrance position, and that the puncture needles 32A and 32B have definitely entered the stomach wall by the observation apparatus 55 in the endoscope 2. In addition, because the distal portion 15 is transparent, the movement of the puncture needles 32A and 32B inside the needle lumens 92 and 93 can be easily observed.

Figure 16:
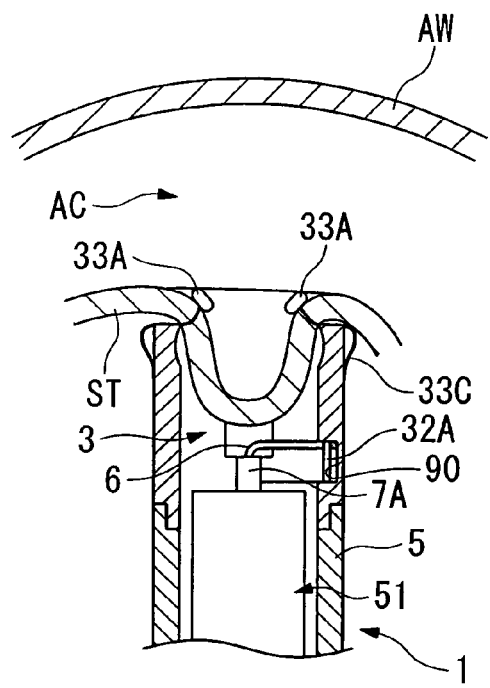
FIG. 16 is a drawing for explaining the state in which the anchors of the two-armed T bar are ejected from the puncture needles during a medical procedure in a first embodiment.

From this state, the pusher connecting portion 43 is advanced towards the needle control handle 41, and the pushers 35 are moved in the direction of the distal end of the puncture needles 32A and 32B. At this time, as shown in FIG. 16, the anchors 33A of the two-arm T bar 33 are pushed by the pushers 35 and delivered from inside the puncture needles 32A and 32B into the abdominal cavity AC (the exit side of the punctured tissue). Here, because the hole 37 is oriented from the proximal end side toward the distal end side of the insertion portion 5, the stopper 33B of the two-arm T bar 33 is inhibited from falling out when not intended. At this time, because the abdominal cavity AC has been insufflated and the space between the abdominal cavity AC and the stomach wall has been established, it is possible to puncture only the stomach wall.

After the anchors 33A of the two-arm T bar 33 are released, the pusher connecting portion 43 is retracted towards the needle control handle 41 to accommodate the pushers 35. Then the puncture needles 32A and 32B are retracted and withdrawn from the stomach wall. At this time, the two anchors 33A of the two-arm T bar 33 are opened in a T-shape due to the bending of the sutures 33C.

Next, the process proceeds to the incision step (S50). First, after the distal end of the endoscope 2 is disposed farther toward the proximal side than the accommodating portion 90, the sheath grip portion 40 is grasped, pulled toward the proximal side, and the puncture needles 32A and 32B are extracted from the distal end portion 15 (or the overtube 1). Because the engagement of the cutting electrode 6 by the puncture needle 32A is released, the cutting electrode 6 is restored so as to traverse the first lumen 3 due to the elastic force thereof. Note that the shape of the cutting electrode 6 may also be restored by moving the electrode controlling wires 7A and 7B forward and backward. This action may also be carried out before the stomach wall suction. Because a space is established that is wider than the distal end portion 15 before the stomach wall suction, there is the effect that the cutting electrode 6 can be easily restored to the center.

Figure 17:
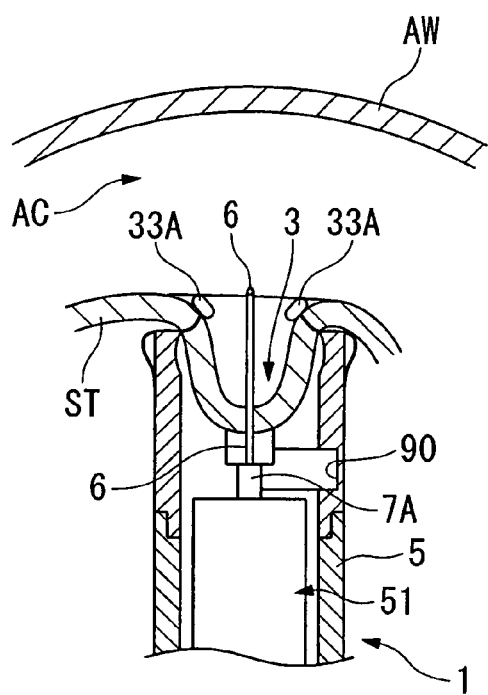
FIG. 17 is a drawing for explaining the state in which an incision is made in the sucked stomach wall by a cutting electrode of the overtube during a medical procedure according to a first embodiment.
Figure 18:
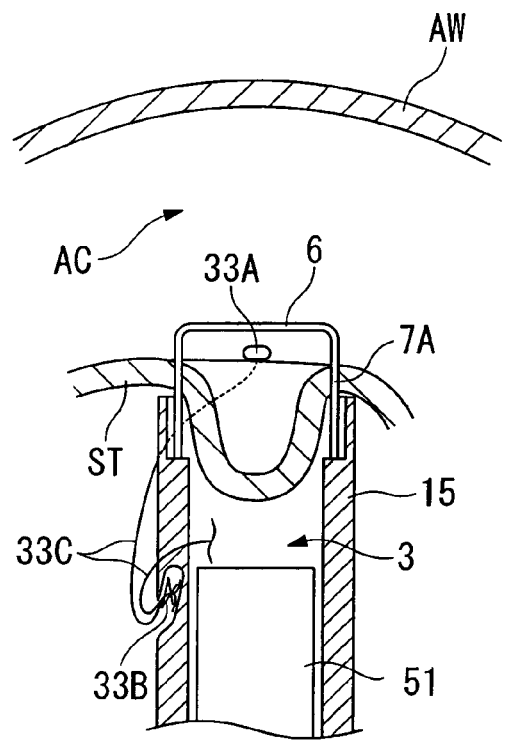
FIG. 18 shows FIG. 17 after being rotated by 90°.

The connection between the connecting terminal 26B of the power cord 28 and the connecting terminal 26A of the electrode controlling portion 8 is confirmed. Then, while supplying high frequency power from the high frequency power source 27, the control handle 21 is advanced toward the control body portion 20, and the cutting electrode 6 is projected from the distal end portion 15 to abut the stomach wall. At this time, because the cutting electrode 6 is energized via the electrode controlling wires 7A and 7B, as shown in FIG. 17 and FIG. 18, the stomach wall is cut open by the cutting electrode 6, and an opening SO is formed in the stomach wall.

Note that in this step as well, the suction on the stomach wall is continued, and thus the retention position of the two-arm T bar 33 and the incision position are in an optimal state.

Next, the process proceeds to a removal step (S60). Here, in order to remove the cutting electrode 6 from the insertion portion 5, the fastening screw 24 on the control body portion 20 of the electrode controlling portion 8 is loosened. At this time, the electrode controlling wires 7A and 7B are separated from the connecting plate 23, and the electrode controlling wires 7A and 7B are detached. Then, for example, by grasping and then pulling the end portion of the electrode controlling wire 7A toward the distal side, the electrode controlling wire 7A is moved through the inside of the first lumen 3 to the proximal end side, and the electrode controlling wire 7B is moved through the inside of the first lumen 3 to the distal end side. Finally, the electrode controlling wire 7B also moves to the proximal end side by passing through the distal end opening of the first lumen 3. In this manner, the cutting electrode 6 is extracted along with the electrode controlling wires 7A and 7B.

Figure 19:
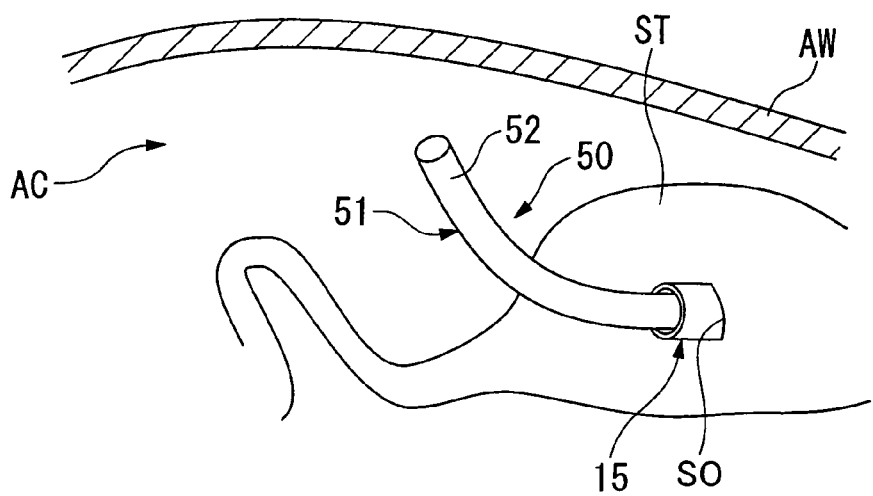
FIG. 19 is a drawing for explaining the state in which the endoscope has been inserted into the abdominal cavity during a medical procedure according to a first embodiment.

Next, the process proceeds to an introduction step (S70). Specifically, as shown in FIG. 19, the endoscope insertion portion 51 of the endoscope 2, which is the treatment device, is introduced into the abdominal cavity AC by passing through the opening SO. At this time, when it is necessary to restrict the relative motion between the insertion portion 5 and the endoscope insertion portion 51, an endoscope lock button 47 is pressed to abut the endoscope insertion portion 51, and due to the friction therebetween, the movement of the endoscope insertion portion 51 is prevented. Because the endoscope lock button 47 is provided, it is possible to inhibit the movement of the endoscope 2 relative to the overtube 1 by operating the endoscope lock button 47, and it is possible to insert both the overtube 1 and the endoscope 2 into the body simultaneously. In addition, because the operation of inserting the endoscope 2 is carried out while holding the proximal handle 44 of the overtube 1, one hand of the operator can support the insertion portion 5 of the overtube 1 while the other hand can carry out the operation of grasping the proximal handle 44, and thereby the operability is further improved.

When the overtube 1 is introduced into the abdominal cavity AC through the opening SO, the retention positions of the anchors 33A of the two-arm T bar 33 become more toward the proximal side than the position of the hole 37 formed in the insertion portion 5. Thereby, the stopper 33B accommodated in the hole 37 is pulled in the direction of separation from the hole 37 due to the orientation of the hole 37, and the stopper 33B drops out of the hole 37.

After positioning, the treatment step (80) is executed in which various treatments (medical procedures) such as observation, incision, cell aspiration, suturing or the like are carried out. After carrying out the treatment, the overtube 1 and the endoscope 2 are removed from the opening SO in the stomach wall.

Figure 20:
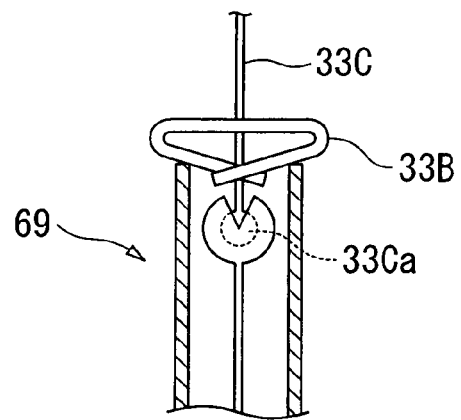
FIG. 20 is a drawing for explaining the state in which the suture of the retained two-armed T bar is pulled and bound during a medical procedure according to a first embodiment.

As shown in FIG. 20, in the suture step (S90), when the endoscope 2 is extracted from the opening SO by a ligating tool 69 that has been inserted into the channel 60 of the endoscope 2, the large diameter portion 33Ca of the suture 33 is grasped and pulled against the stopper 33B of the two-arm T bar 33 that has been retained in advance. In this manner, the opening SO is sutured. Note that depending on necessity, further suturing is carried out by adding a two-arm T bar 33. At this time, first because the abdomen is insufflated when the two-arm T bar 33 is retained on the stomach wall, suturing by an additional two-arm T bar 33 can be carried out easily.

After suturing, the endoscope 2 is removed from the patient, the pressure applied to the abdominal cavity AC is released, and the procedure is completed.

According to this overtube 1, because a cutting electrode 6 can be disposed on the distal end side of the insertion portions by traversing the distal end side of the first lumen 3, when the insertion portion 5 is inserted into the stomach ST, it is possible to cut the stomach wall open without preparing special incision instruments. Because it is possible to cut a length of tissue equivalent to the length of the cutting electrode 6 that traverses the first lumen 3, it is possible to pass the overtube 1 with a light force, and it is possible to inhibit leaks at the outer periphery of the overtube 1 advantageously. In addition, because an accommodation portion 90 is provided and the cutting electrode 6 is accommodated so as not to project into the first lumen 3, the extension and retraction of the device (in this embodiment, the endoscope 2) and the visual field of the observation apparatus provided on the device can be ensured. Furthermore, because it is possible to project the device from the distal end of the overtube 1, the character of insertion into the body can be further improved.

Because the electrode controlling wires 7A and 7B can be separated from the electrode controlling portion 8, the cutting electrode 6 can be removed from the insertion portion 5 along with the electrode controlling wires 7A and 7B. Therefore, after forming the opening SO, when the endoscope 2 projects from the first lumen 3, the cutting electrode 6 is not an obstruction, and when the endoscope 2 passes through the first lumen 3, the endoscope 2 can be advanced farther into the abdominal cavity AC past the tissue that has been cut open. Furthermore, after forming the opening by cutting the tissue, when the device (in this embodiment, the endoscope 2) that has passed through the first lumen 3 advances to project from the distal end of the overtube 1, the operation of retracting the cutting electrode 6 from the passage of the device and the operation of removing the cutting electrode 6 by temporarily removing the overtube 1 from the body can be omitted. As a result, it is possible to reduce the time for the procedure up to introducing the endoscope 2 into the abdominal cavity AC after opening the stomach wall.

In addition, because the cutting electrode 6 is connected to the electrode controlling wires 7A and 7B, which can be operated so as to advance into or retract from the first lumen 3, it is possible for the cutting electrode 6 to be advanced and retracted in the first lumen 3 without advancing or retracting the entire insertion portion 5. That is, it is possible to cut by advancing and retracting the cutting electrode 6 with respect to the stomach wall by advancing and retracting the electrode controlling portion 8. At this time, because cutting is carried out while conducting a high frequency current through the cutting electrode 6, it is possible to cut safely using a light force.

In addition, it is possible to retain the anchors 33A by engaging the sutures 33C before forming the opening by cutting the wall (in this embodiment, the stomach wall) of the abdominal organs. Here, because the long hole 30 (the opening through which the puncture needles 32A and 32B project) is disposed inside the distal end portion, the operating conditions of the puncture needles 32A and 32B can be more easily confirmed by the observation apparatus provided on the device. In addition, because the projection direction of the puncture needles 32A and 32B is controlled by projecting the puncture needles 32A and 32B along the guide portions 91 from the long holes 31 toward the front of the first lumen 3 in the axial (center axis) L3 direction, it is possible to insert the puncture needles 32A and 32B into the tissue while a space is established between the inner surface of the distal end portion 15 and the position at which the needles 32A and 32B puncture the tissue. In other words, it is possible to set the entrance position of the puncture needles 32A and 32B to a portion (farther inside than the abutting position 15B of the distal end portion 15) separated from the end portion of the tissue that is held inside the first lumen 3 by suction. Thus, when the puncture needles 32A and 32B are inserted, the tissue (in this embodiment, the stomach wall) is not easily detached. In the case of a structure that differs from this embodiment, for example, a structure in which the puncture needles advance and retract farther outside (the outer surface side) than the distal end opening or a structure having an opening through which the puncture needles extend or retract in the portion abutting the distal end portion, it is difficult for the puncture needles to enter the tissue that is being sucked while the abutting portion of the distal end portion abuts the tissue. In addition, the operational condition of the puncture needles is difficult to confirm. However, in this embodiment, such problems are solved and the operability is improved.

Furthermore, because the anchors 33A are retained and the sutures 33C pass through the stomach wall before forming the opening (before suturing), when the targeted incision site T is cut open by the cutting electrode 6, movement of the tissue is prevented, and thereby cutting can be carried out more reliably. In addition, this is possible in a state in which the sutures 33C are only bound during suturing. When the opening is sutured after the medical procedure in the abdominal cavity AC has been completed, it is possible to carry out the suturing of the opening more easily without insulating the stomach, and thereby the suturing operation becomes easier. Here, when the puncture needles 32A and 32B are not used, it is possible to accommodate the puncture needles 32A and 32B in the needle lumens 92 and 93 formed in the distal end portion 15, and thus the puncture needles 32A and 32B do not interfere when a device such as the endoscope 2 are being operated.

In addition, because the direction in which the cutting electrode 6 traverses the first lumen 3 is perpendicular to the direction at which the puncture needles 32A and 32B are joined to the cutting electrode 6, it is possible to separate the puncture position of the puncture needles 32A and 32B from the incision location.

Figure 21:
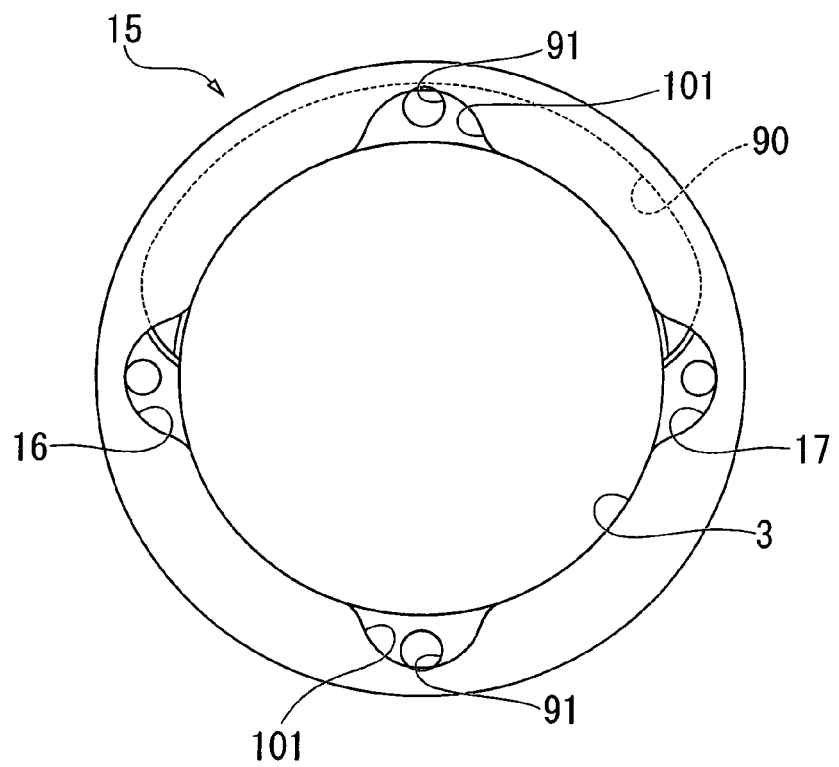
FIG. 21 is a frontal view of the distal end portion showing a modified example.
Figure 22:
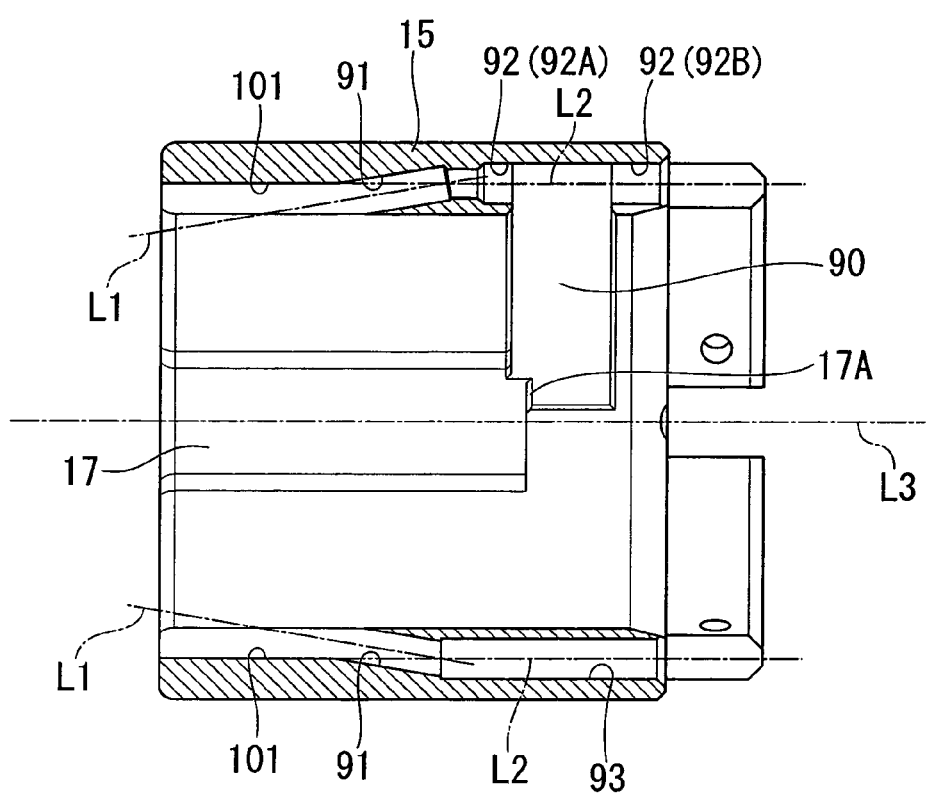
FIG. 22 is a cross-sectional view along the V-V line in FIG. 21.

Here, modified examples are shown in FIG. 21 and FIG. 22. A notched portion 101 is formed in the distal portion 15 by cutting a portion of the inside periphery that includes the guide portion 91. The notched portion 101 is formed only in the vicinity of the guide portion 91, but may extend up to the vicinity of the inner grooves 16 and 17. Due to the notched portion 101, a larger space can be established the around of the puncture needles 32A and 32B, or in other words, the space between the entry position of the puncture needles 32A and 32B and the inner surface of the distal end portion 15. Because it is possible to suck more tissue in the region around the puncture needles 32A and 32B, there is the advantage that the tissue does not easily detach during puncture.

Note that in this embodiment, a structure and method were explained in which the cutting electrode 6 is accommodated in the accommodation portion 90 by being held back by the puncture needles 32A and 32B. However, in the case that there is a sufficient gap between the overtube 1 and the endoscope 2, the cutting electrode 6 may be disposed between the overtube 1 and the endoscope 2 without being accommodated in the accommodating portion 90, and thus the endoscope 2 may project from the overtube 1 to improve the characteristics of the insertion into the body.

At this time, because there is a possibility that the cutting electrode 6 may be pressed by the endoscope 2 and have a bend imparted thereto when the endoscope 2 is moved relative to the overtube 1, the cutting electrode 6 is accommodated and protected in the electrode tubes 18. Instead, the electrode controlling wires 7A and 7B may be exposed and the cutting electrode 6 exposed from the electrode tubes 18 and used only when cutting tissue (the stomach wall). When done in this manner, it is possible to protect the cutting electrode 6 during insertion into the body, it is possible to decrease the possibility that a bend will be imparted to the cutting electrode 6, and thereby the shape of the cutting electrode 6 will be in the desired condition while making an incision.

An example of a method in which the cutting electrode 6 is accommodated in the electrode tubes 18 and exposed while making an incision is to detach one electrode tube 18 from the electrode controlling portion 8 and push out the electrode tube 18 while pressing the control handle 21. When done in this manner, only one electrode controlling wire is pressed and exposed from the electrode tubes 18, and at the other electrode controlling wire, the cutting electrode 6 is accommodated by being pressed by the electrode tube 18. When in use, while pulling the control handle 21, the electrode tubes 18 are pulled to expose the cutting electrode 6, and the electrode tubes 18 are fastened again to the electrode controlling portion 8. By carrying out the operation in this manner, the advance and retraction operation (and protection) of the cutting electrode 6 becomes possible.

Second Embodiment

A second embodiment of the present invention will be explained with reference to the drawings.

Figure 23:
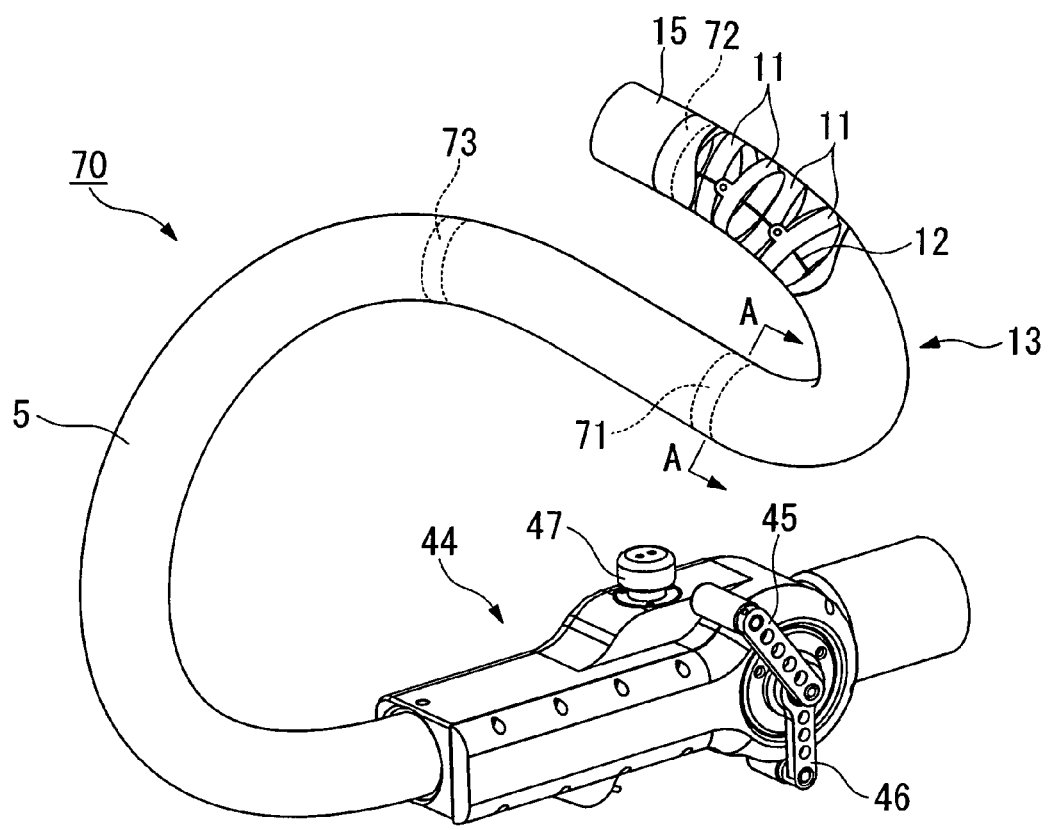
FIG. 23 is a drawing showing the essential portions of the overtube according to a second embodiment.
Figure 24:
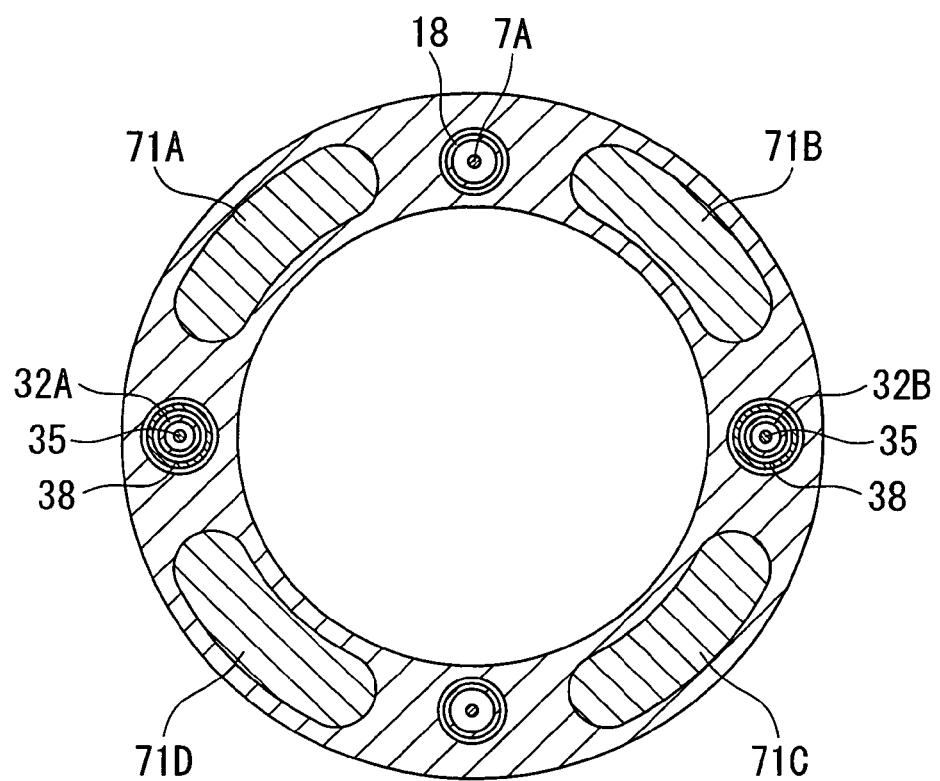
FIG. 24 is a cross-sectional view along line A-A in FIG. 21.

The second embodiment differs from the first embodiment on the point that in this embodiment, as shown in FIG. 23, the overtube 70 provides a first magnet (magnetic body) 71 that is disposed on the outer peripheral surface of the insertion portion 5 in proximity to the proximal end of the bent portion 13; a second magnet (magnetic body) 72 that is disposed on the outer peripheral surface of the distal end side of the bent portion 13; and a third magnet (magnetic body) 73 that is disposed more toward the proximal end side (the control handle 21 side) of the insertion portion 5 than the first magnet 71. Because the enlargement of the insertion portion 5 of the overtube 70 is inhibited while the inner diameter of the first lumen 3 is secured, as shown in FIG. 24, the first magnet 71 (identical to the second magnet 72 and the third magnet 73) is disposed by being partitioned, for example, into magnetic pieces 71A, 71B, and 71C at locations other than the locations where the electrode tubes 18 that pass through the insertion portion 5 and the outside sheath 38 are disposed.

In addition, these magnets 71, 72, and 73 are formed such that the outer peripheral surfaces all have identical magnetic poles. For example, when the first magnet 71 is the S-pole, the magnetic poles are alternately arranged along the insertion portion 5 such that the second magnet 72 and the third magnet 73 are N-poles.

Figure 25:
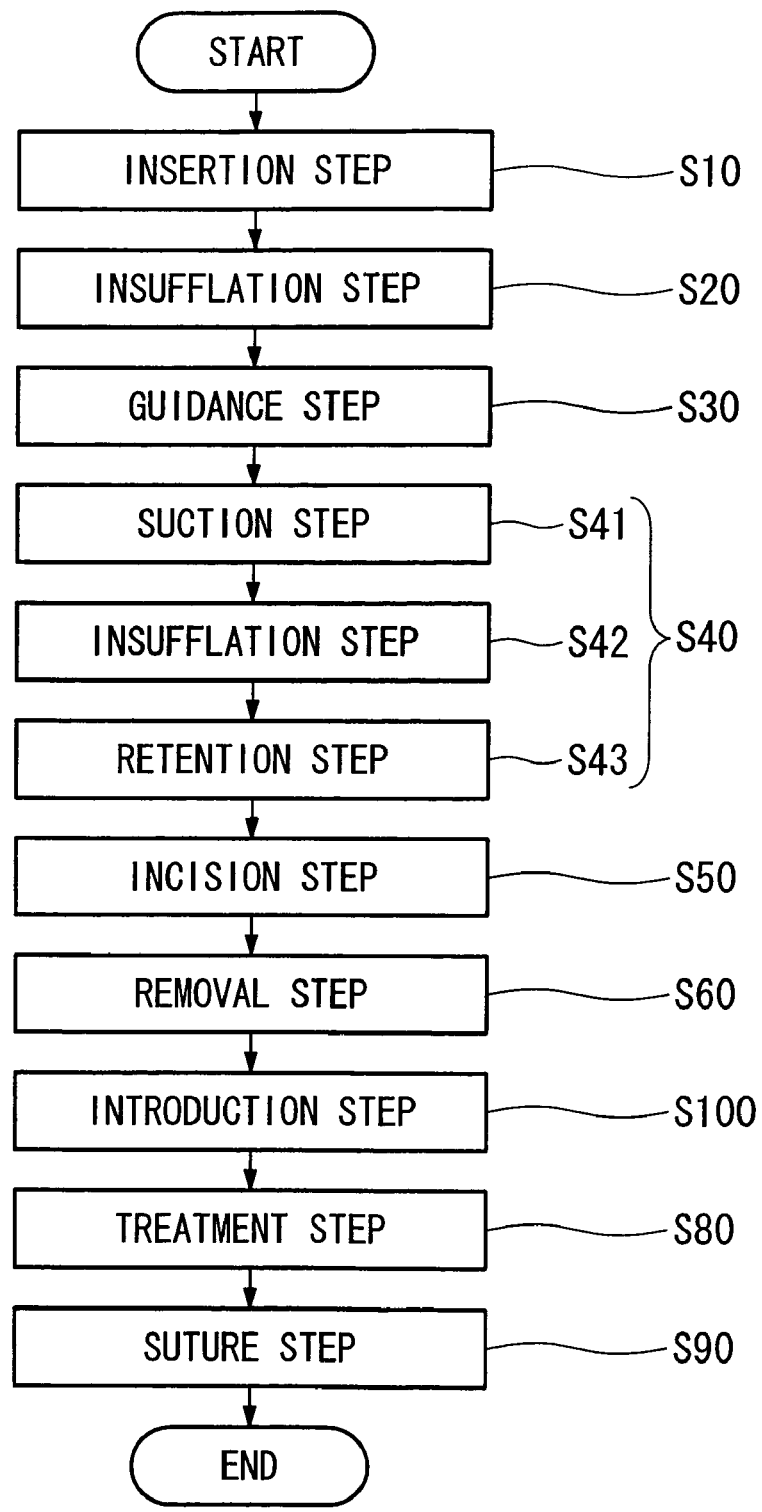
FIG. 25 is a flowchart for a medical procedure according to a second embodiment.

Next, the operation of this embodiment will be explained along with a method for a medical procedure through a natural orifice shown in the flowchart in FIG. 25 using the overtube 70.

In this embodiment, steps from the insertion step (S10) to the removal step (S60) identical to those in the first embodiment are executed.

Next, the process proceeds to the introduction step (S100). Specifically, as shown in FIG. 19, the endoscope insertion portion 51 of the endoscope 2 is inserted into the abdominal cavity AC through the opening SO.

Figure 26A:
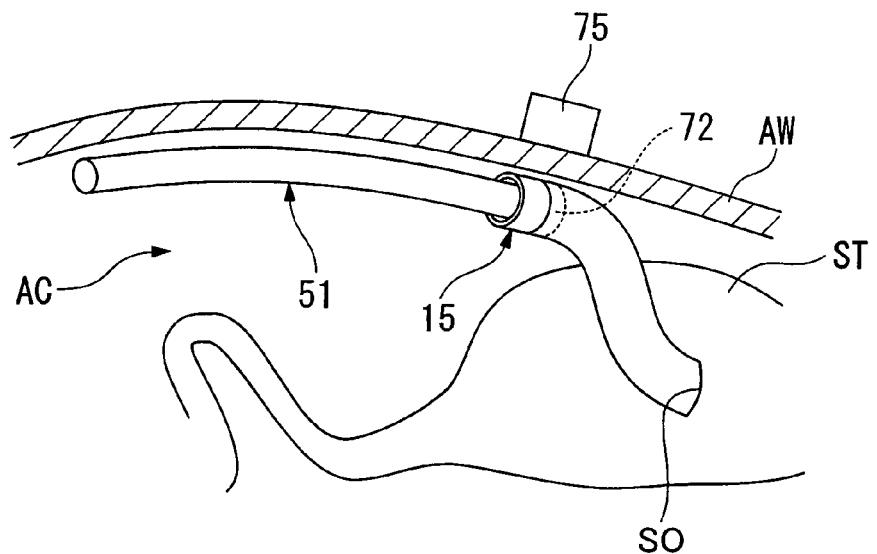
FIG. 26A is a drawing for explaining the state in which the endoscope insertion portion projects from the overtube during a medical procedure according to a second embodiment.
Figure 26B:
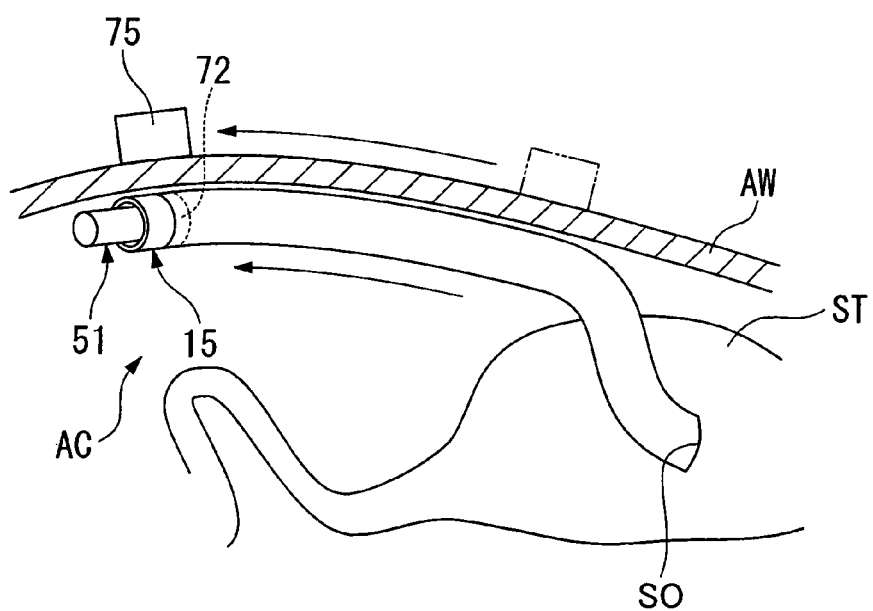
FIG. 26B is a drawing for explaining the state in which the overtube is moved from the state shown in FIG. 26A within the abdominal cavity by using a second magnet of the overtube, where the endoscope insertion portion acts as a guide.
Figure 27A:
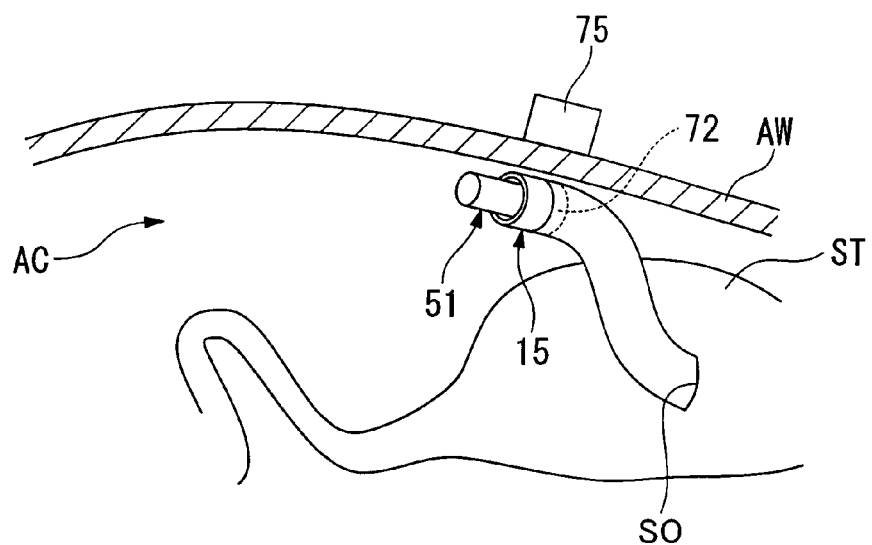
FIG. 27A is a drawing for explaining the state in which the endoscope insertion portion and the overtube both project from the opening during a medical procedure according to a second embodiment.
Figure 27B:
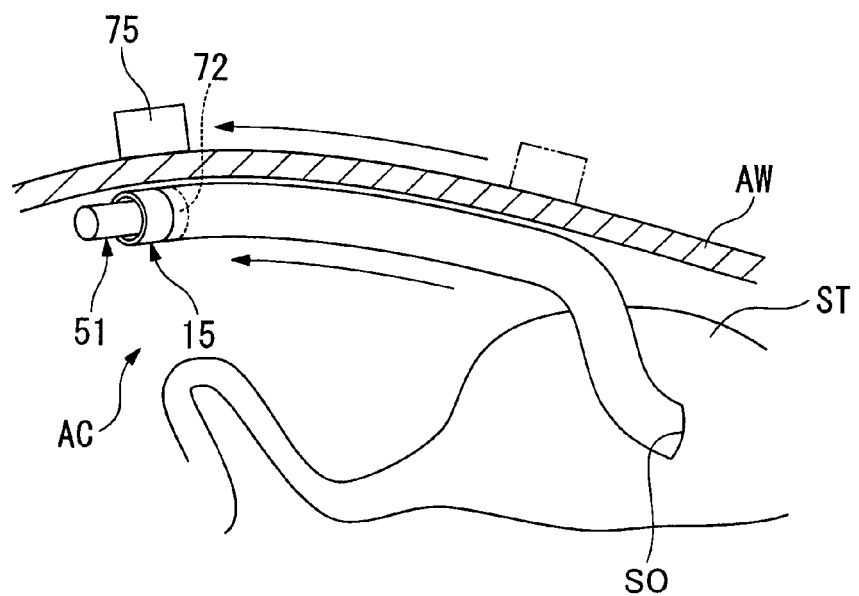
FIG. 27B is a drawing for explaining the state in which the endoscope insertion portion and the overtube are moved within the abdomen from the state shown in FIG. 27A by using a second magnet of the overtube.

In addition, as shown in FIG. 26, while the distal end portion 15 of the overtube 70 projects from the opening SO in the stomach ST, a moving magnet 75 is mounted on the stomach wall AW in proximity to the opening SO such that the magnetic poles of the moving magnet 75 and the second magnet 72 of the overtube 70 attract each other. At this time, the moving magnet 75 and the second magnet 72 attract each other. Next, the moving magnet 75 is moved along the abdominal wall AW up to the position that the treatment position is located. At this time, the distal end portion 15 moves while being attracted to the moving magnet 75. At this time, as shown in FIG. 26A, the endoscope insertion portion 51 has been advanced beforehand beyond the insertion portion of the overtube 70, and as shown in FIG. 26B, the distal end portion 15 of the overtube 70 may be advanced along the endoscope insertion portion 51 toward the distal end of the endoscope insertion portion 51 by using the moving magnet 75. In addition, as shown in FIG. 27A, the moving magnet 75 may be moved while the endoscope insertion portion 51 is accommodated inside the overtube 70, and as shown in FIG. 27B, the endoscope insertion portion 51 may be moved along with the overtube 70.

Figure 28:
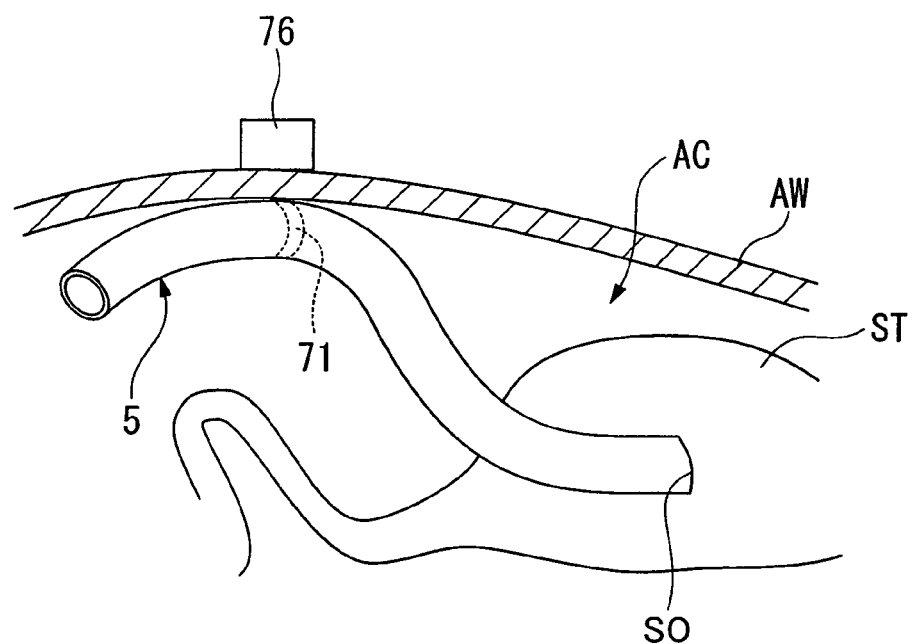
FIG. 28 is a drawing for explaining the state in which the overtube is supported inside the abdomen by using a first magnet of the overtube during a medical procedure according to a second embodiment.
Figure 29:
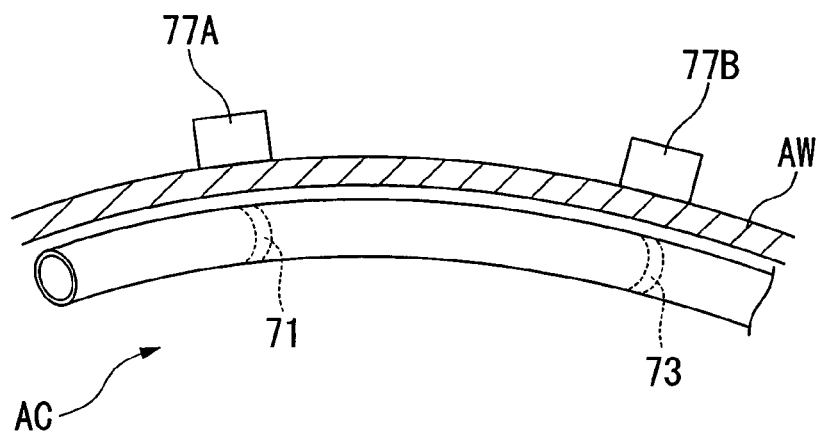
FIG. 29 is a drawing for explaining the state in which the direction of the overtube in the abdominal cavity is changed by using a first magnet and a third magnet of the overtube during a medical procedure according to a second embodiment.

As shown in FIG. 28, in order to establish the bent shape of the bent portion 13, a stationary magnet 76 is mounted on the abdominal wall AW such that the stationary magnet 76 and the first magnet 71 attract each other. At this time, because the stationary magnet 76 and the first magnet 71 attract each other, the bending operation is carried out by operating the bending control lever 45 while the insertion portion 5 is held and supported on the abdominal wall AW. Here, when the direction of the distal end portion 15 changes while the bent state of the insertion portion 5 is maintained, the support magnets 77A and 77B are mounted on the abdominal wall AW. Specifically, the support magnet 77A and the first magnet 71 attract each other and the support magnet 77B and the third magnet 73 attract each other. As shown in FIG. 29, when in these respective attractive states, for example, by fastening the third magnet 73 and rotating the first magnet 71 centered on the third magnet 73, the direction of the distal end portion 15 is changed.

Subsequently, after executing the treatment step (S80), the endoscope 2 is returned inside the stomach ST through the opening SO in the stomach wall, removed from the mouth M of the patient PT, and the process moves to the suture step (S90). Then the opening SO in the stomach wall is sutured.

After suturing, the endoscope 2 is removed from the patient, the pressure applied to the abdominal cavity AC is released, and the procedure is completed.

According to this overtube 70, actions and effects identical to those of the first embodiment are exhibited. In particular, because the first magnet 71, the second magnet 72, and the third magnet 73 are disposed externally on the insertion portion 5, due to the attraction between the moving magnet 75, the stationary magnet 76, and the support magnets 77A and 77B, the insertion portion 5 can be supported on the abdominal wall AW. Therefore, it is possible to prevent advantageously the endoscope 2 from becoming displaced during treatment while inserted into the overtube 70. In addition, by moving the moving magnet 75, it is possible to move the distal end direction of the endoscope 2, which has been inserted into the overtube 70, easily by using the magnets, and thereby it is possible to carry out control of the direction of the endoscope 2 easily. In addition, by using the moving magnet 75, the stationary magnet 76, and the support magnets 77A and 77B, the movement, fastening, and support of the overtube 70 can be carried out from outside the body, and the overtube 70 becomes easier to orient.

Note that the technical scope of the present invention is not limited by the embodiments described above, and various modifications can be made that do not depart from the spirit of the present invention.

For example, in the embodiments described above, a flexible endoscope was used as the observation apparatus. However, this is not limiting, and for example, what is called a capsule endoscope may be retained inside the body, and while observing the inside of the body using the same, the desired procedure may be carried out by passing the insertion portion of a treatment device that does not have an observation apparatus through the overtube.

In addition, the number of puncture needles is not limited to two. Four or six puncture needles may be disposed at predetermined intervals in the peripheral direction. It is possible to ensure a plurality of suture locations in the incision direction, and thereby it is possible to carry out the suturing more reliably.

Figure 30:
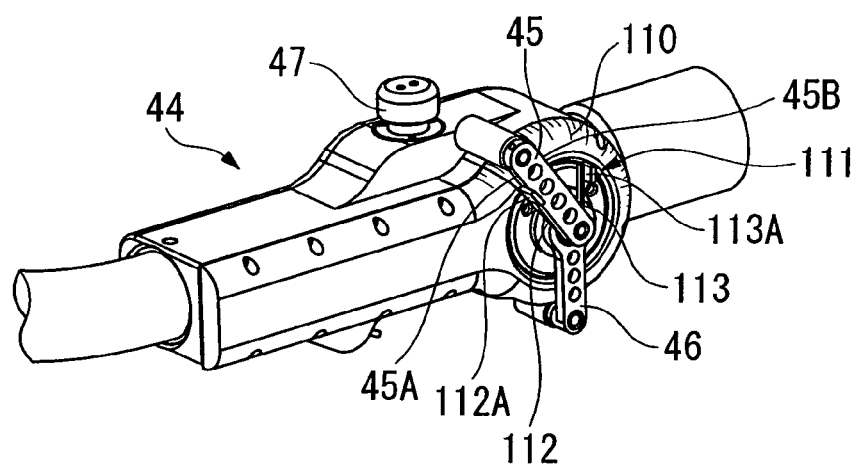
FIG. 30 is a perspective view in which a scale and a scale-detecting member are provided on the proximal handle.

As shown in FIG. 30, a scale 110 may be provided on the side portion of the proximal handle 44 along the movement path of the bending control lever 45. By confirming the scale 110, the condition of the bending can be easily grasped. Furthermore, a scale detecting apparatus 111 may be provided. The scale detecting apparatus 111 has a first lever 112 and a second lever 113 disposed so as to surround the operation direction of the bending control lever 45. The first lever 112 provides an engaging piece 112A that can abut the side surface 45A of the curvature controlling levers 45. The second lever 113 provides an engaging piece 113A that can abut the other side surface 45B of the bending control lever 45. The respective levers 112 and 113 are provided freely rotatably coaxial to the bending control lever 45. An example of a supporting structures for the levers 112 and 113 are a rotating axle of the bending control lever 45, a tube separately inserted freely rotatably between the levers 112 and 113 and the cover of the proximal handle 44, and a flexible member that is fastened in the tube and that produces a prescribed frictional force between the levers 112 and 113 and the cover of the proximal handle 44.

Figure 31:
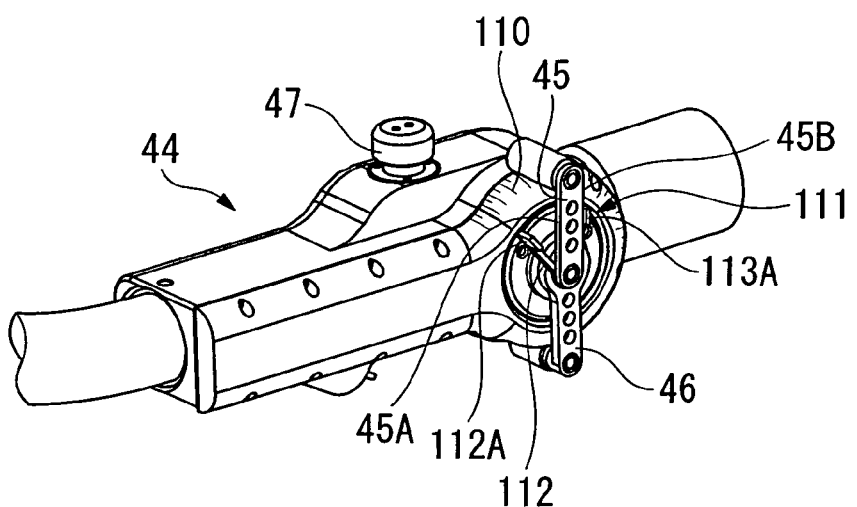
FIG. 31 is a drawing for explaining the operation of the scale-detecting member.

In FIG. 30, the curvature control lever 45 is inclined at a first angle. From this state, as shown in FIG. 31, when the curvature control lever 45 is rotated, the engagement of the first lever 112 with the engaging piece 112A is released. Because the first lever 112 is provided separately from the curvature control lever 45 and is supported by a prescribed frictional force on the proximal handle 44, the first lever 112 stops and remains at the first angle. Even when the curvature control lever 45 is returned, it is possible to confirm the first angle from the position of the first lever 112.

An example of the usage of such a scale detection apparatus 111 is switching the endoscope 2 after introducing the overtube 1 and the endoscope 2 into the body and bending them to the first angle. When the bent portion 13 of the overtube 1 is greatly bent (that is, when bent to a small radius of curvature), the bent portion 15 returns temporarily to a gently bent shape or a rectilinear shape, it is then possible to replace the endoscope 2, and the replacement action can be carried out smoothly. After inserting a new endoscope 2, if the curvature control lever 45 is returned to the position of the first lever 112, the curvature angle that was determined first, that is the position of the distal end portion, can be made again. Note that in the meantime, the second lever 113 does not engage with the curvature control lever 45, and stops in the initial position. When the overtube 1 is bent toward the opposite side, the second lever 113 is operated as described above.

In addition, by operating the curvature control lever 45, the bent portion 13 is provided in two directions (two directions, wherein the insertion portion 5 is opposite to the substantially rectilinear state). However, two curvature control levers 45 may be provided to enable bending in 4 directions.

Figure 32:
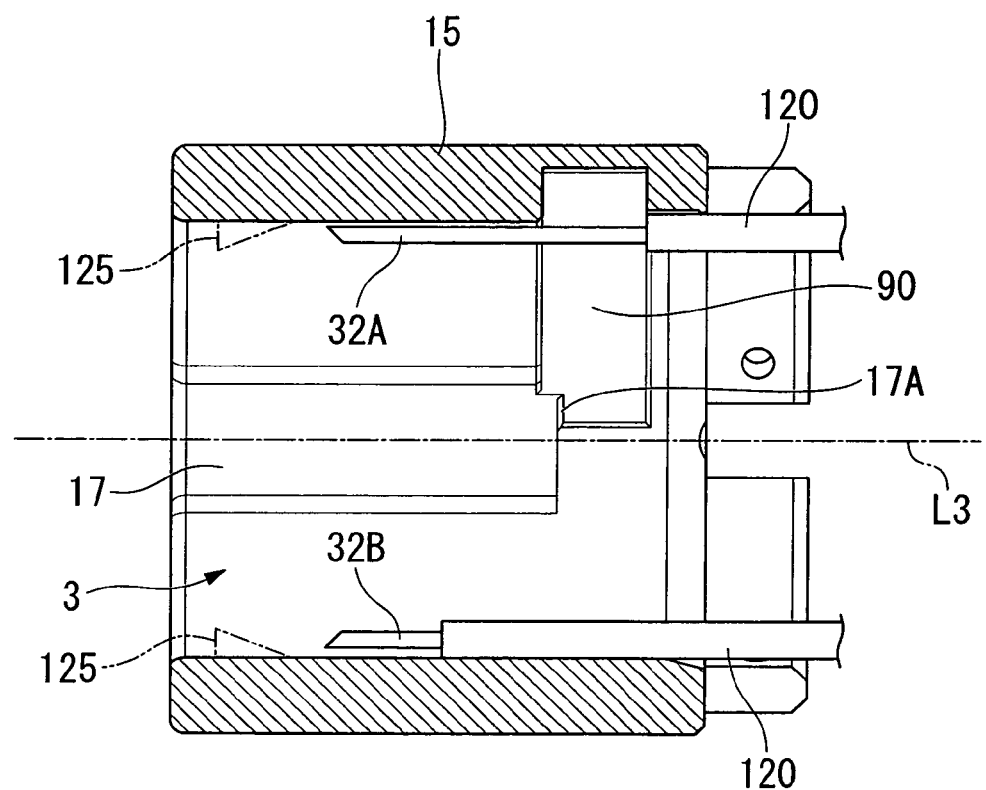
FIG. 32 is a cross-sectional view showing an example of a modification in which the needle lumens are established along the inside perimeter of the lumen.

As shown in FIG. 32, a needle lumen 120 (second lumen) may be fastened along the inner surface that forms the first lumen 3. Puncture needles 32A and 32B may each pass so as to be freely extendable and retractable in the needle lumen 120. Because it is possible to enter tissue that is drawn from the distal end opening of the first lumen 3, effects identical to those described above can be obtained. In this case, as shown by the imaginary line in FIG. 32, when a projection shaped or taper shaped guide portion 125 that projects on the distal end or inside is provided on the inner periphery of the distal end portion 15 on the movement path of the puncture needles 32A and 32B, because the puncture needles 32A and 32B are urged inside by the guide portion, it is possible to set the entrance position more toward the center.

What is claimed is:

1. An overtube comprising:
   an insertion portion that has a distal end portion and a proximal end portion, and at least the distal end portion thereof is adapted to be inserted into a subject;
   a first lumen that is formed in the insertion portion and that allows freely inserting and removing a device for carrying out medical procedures in the subject;
   puncture needles that pass through the insertion portion, have a control member connected to the proximal end portion of the insertion portion, and are adapted to puncture tissue; and
   one or more second lumens provided inside the first lumen, through which one or more of the puncture needles are passed, a distal portion of each of the one or more second lumens having an opening at a distal side of the first lumen,
   wherein the distal portion of each of the one or more second lumens has a direction with at least a radially inward component.

2. The overtube according to claim 1, wherein an opening is formed on the distal end portion of the insertion portion so as to communicate with the first lumen in order to project the device in the forward insertion direction for insertion into the subject.

3. The overtube according to claim 1, wherein an abutting portion formed at a distal end of the distal end portion of the insertion portion is adapted to abut the tissue when the tissue of the subject is sucked.

4. The overtube according to claim 2, further comprising a guide portion that controls the projection direction of the puncture needles that project from the openings of the second lumens and that makes the puncture needles project in a center direction of the first lumen that is in cross-section substantially perpendicular to the direction in which the distal end portion of the insertion portion connects the proximal end portion of the insertion portion.

5. The overtube according to claim 2, wherein a distal end area of the second lumens has a passage that angles the puncture needles from the proximal end portion to the distal end portion from the inner surface of the distal end portion that forms the first lumen to the direction of the center axis of the first lumen.

6. The overtube according to claim 3, wherein each puncture needle has a passage therein that can accommodate an anchor that is to be disposed on an exit side of a punctured tissue.

7. The overtube according to claim 6, wherein the puncture needles include a first puncture needle and a second puncture needle, each of the puncture needles being disposed at opposing positions across the approximate center of the first lumen.

8. The overtube according to claim 7, wherein the anchors accommodated in the first puncture needle and the second puncture needle are connected together by a thread, and the distal end has a hole which accommodates a stopper portion provided on the thread.

9. The overtube according to claim 2, wherein a notched portion is formed in an inside periphery of the distal end portion.

10. The overtube according to claim 2, wherein, at the distal end portion of the insertion portion, the second lumens are formed inside the distal end portion, and centers of the openings of the second lumens are formed in the inner side of the distal end portion of the first lumen more towards the proximal side than the opening of the insertion portion.

11. The overtube according to claim 1, wherein the distal portion of each of the one or more second lumens is offset with regard to an axial direction of the first lumen.

* * * * *